(12) United States Patent
Morgenshtein et al.

(10) Patent No.: US 7,544,979 B2
(45) Date of Patent: Jun. 9, 2009

(54) ION CONCENTRATION TRANSISTOR AND DUAL-MODE SENSORS

(75) Inventors: Arkadiy Morgenshtein, Kiryat Motzkin (IL); Uri Dinnar, Haifa (IL); Yael Nemirovsky, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 795 days.

(21) Appl. No.: 10/825,123

(22) Filed: Apr. 16, 2004

(65) Prior Publication Data

US 2005/0230245 A1     Oct. 20, 2005

(51) Int. Cl.
*G01N 27/00* (2006.01)
*G01N 27/414* (2006.01)

(52) U.S. Cl. .................... 257/253; 204/416; 422/82.03; 438/142

(58) Field of Classification Search ................ 204/416; 422/82.03; 438/142; 257/253
See application file for complete search history.

(56) References Cited

U.S. PATENT DOCUMENTS

| | | | | |
|---|---|---|---|---|
| 4,332,658 A | * | 6/1982 | Tsuboshima | ................ 204/419 |
| 4,444,644 A | * | 4/1984 | Hiramoto et al. | ............ 204/406 |
| 4,743,954 A | * | 5/1988 | Brown | ........................ 257/253 |
| 6,794,197 B1 | * | 9/2004 | Indermuhle et al. | ......... 436/174 |

OTHER PUBLICATIONS

Morgenshtein, Arkadiy, "Design and Methodology of ISFET (Ion Sensitive Field Effect Transistor) Microsystems for Bio-Telemetry", Master of Science Thesis, Submitted to the Senate of The Technion—Israel Institute of Technology, Haifa, Israel, Apr. 2003.*

Sawada, Kazuaki, et al. "Novel Fused Sensor for Photo and Ion Sensing", Transducers 2003 Proceedings, The 12th International Conference on Solid-State Sensors, Actuators, and Microsystmes, Jun. 8-12, 2003., pp. 1023-1026.*

Morgenshtein et al, "ISFET Operation in Pass-Transistor Mode without Readout Circuits", Proc. of Eurosensors, 17th European Conference on Solid-State Transducers, Portugal, pp. 145-148, Sep. 2003.

Morgenshtein et al, "Combined pH-Image Sensor based on Pass-Transistor Operation of ISFET", Proc. of Eurosensors, 17th European Conference on Solid-State Transducers, Portugal, pp. 1132-1135, Sep. 2003.

Bergveld et al, "Analytical and Biomedical Applications of Non-Selective Field-Effect Transistors", Chap. 8, from "Comprehensive Analytical Chemistry", G. Svehla, Ed., vol. XXIII, Elsevier, NY,NY, 1988.

Jakobson, C., "Ion Sensitive Field Effect Transistors in Standard CMOS For Brain Monitoring", Research Thesis, The Technion, Israel, 2001.

Casans et al, "Circuit Provides Constant Current for ISFETs/MEMFETs", Design Ideas, Oct. 2000, p. 164.

Morgenshtein "Design and Methodology of ISFET (Ion Sensitive Field Effect Transistor) Microsystems for Bio-Telemetry", Presentation of Lecture in the Department of Biomedical Engineering, Technion—Israel Institute of Technology, Haifa, IL, 45 P., Mar. 2003.

* cited by examiner

*Primary Examiner*—Alex Noguerola
*Assistant Examiner*—J. Christopher Ball

(57) ABSTRACT

An ion concentration sensor produces a signal reflective of the ion concentration within a solution. The ion concentration sensor is based on an ion sensitive transistor having a solution input, a reference input, a diffusion input, and a diffusion output. The ion sensitive transistor is connected as a pass transistor, such that the diffusion output provides an electrical signal indicating an ion concentration in a solution contacting the solution input.

44 Claims, 32 Drawing Sheets
(12 of 32 Drawing Sheet(s) Filed in Color)

Figure 1 – Prior art

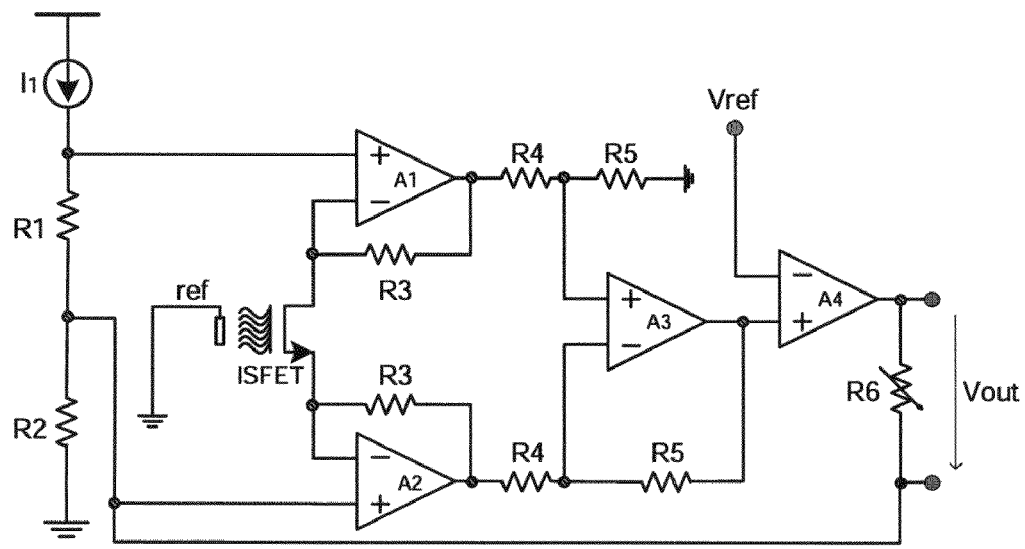
Figure 3 – Prior art

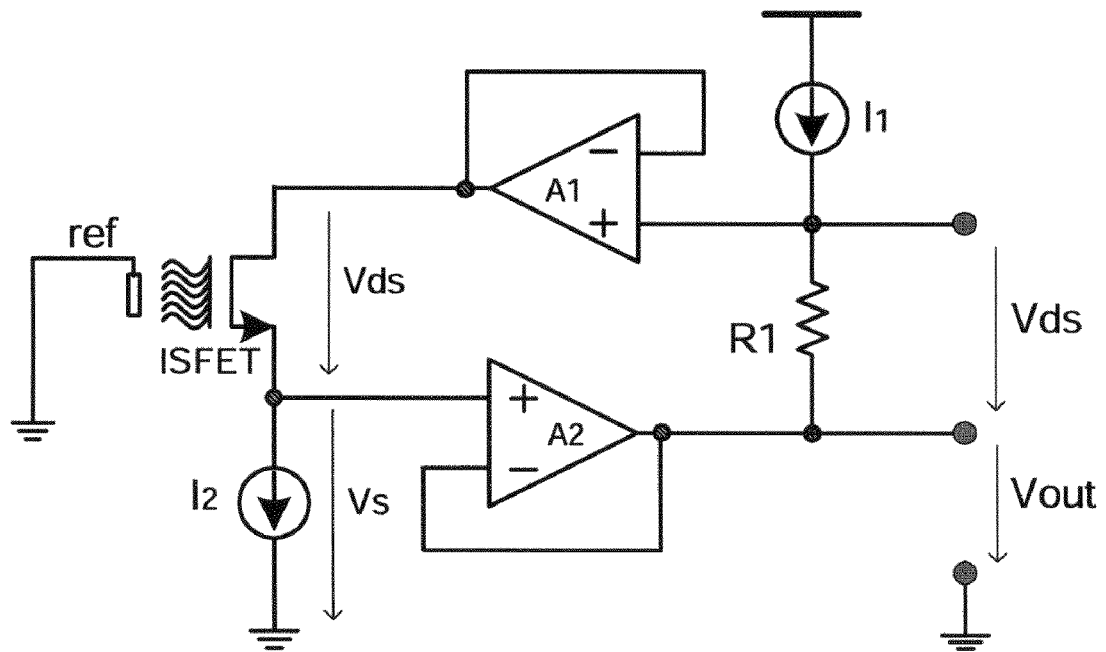
Figure 4a – Prior art

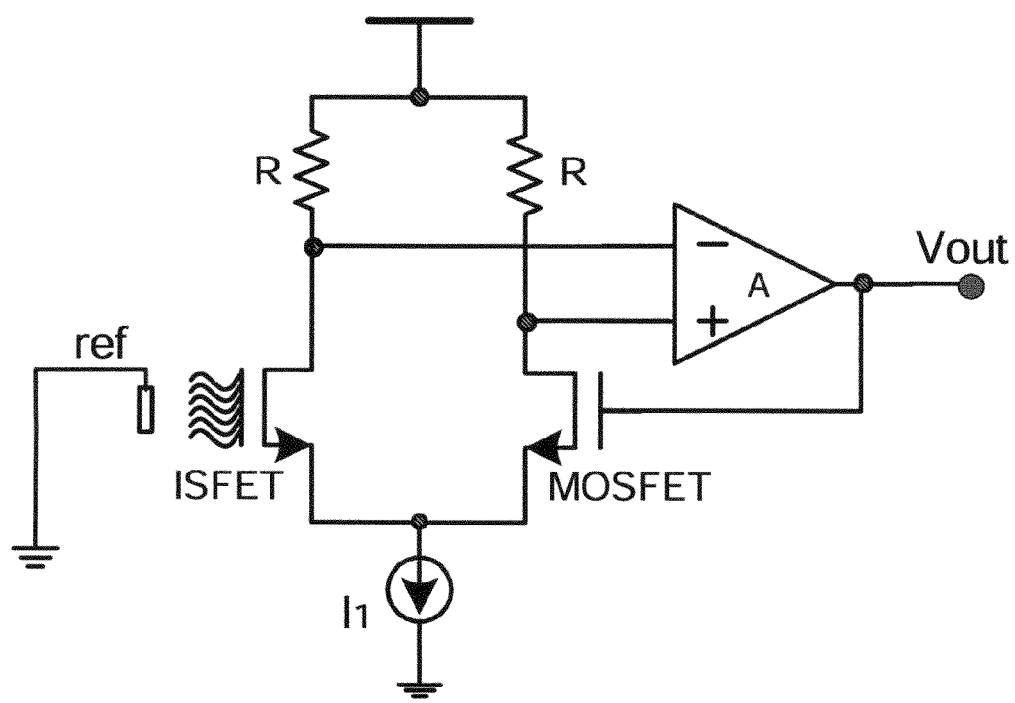
Figure 4b – Prior art

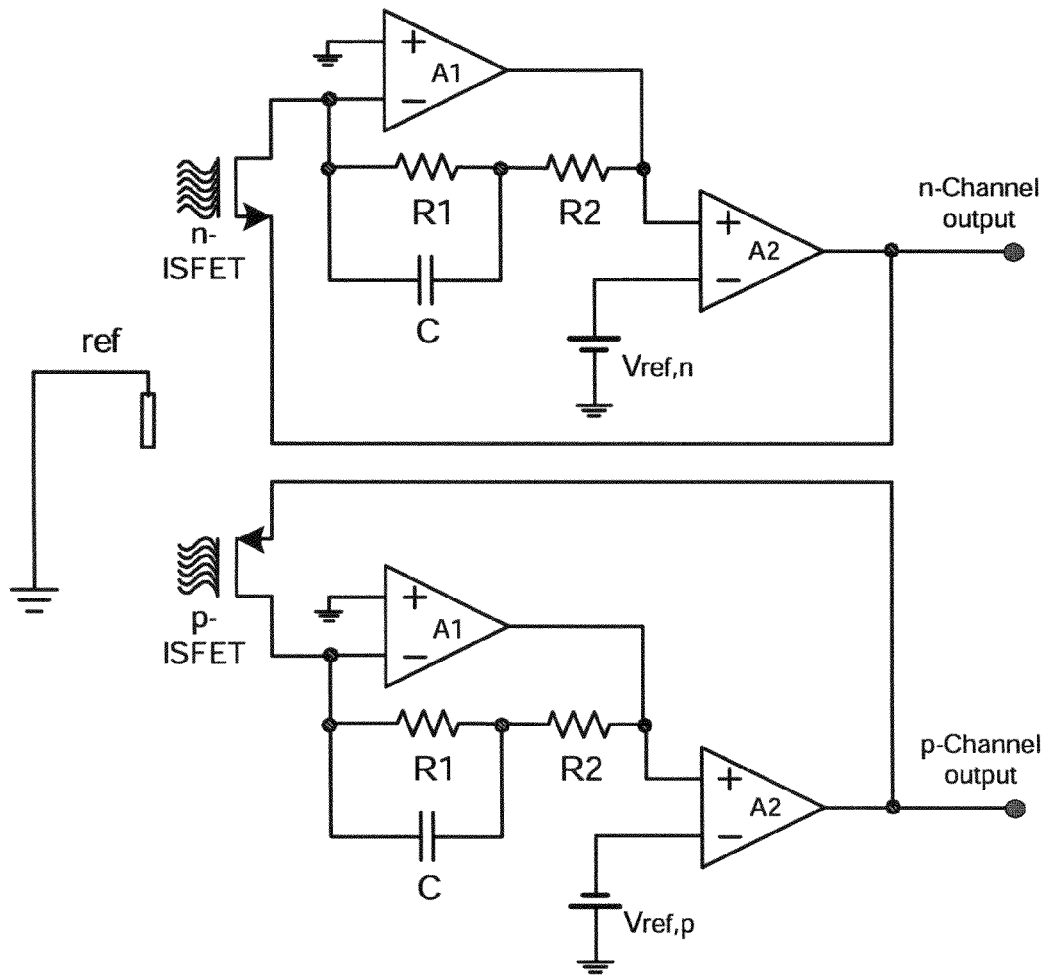
Figure 4c – Prior art

ION CONCENTRATION TRANSISTOR AND DUAL-MODE SENSORS

FIELD AND BACKGROUND OF THE INVENTION

The present embodiments relate to an ion concentration sensor, and, more particularly, an ion concentration sensor based upon an ion sensitive transistor.

Ion concentration measurements, particularly pH (potential of Hydrogen) measurements, are performed routinely in the chemical, biochemical, biomedical, and other fields. In the biomedical field, for example, a pH sensor may be used during neurosurgery to perform brain monitoring via CSF, blood pH measurement, and biotelemetry. A variety of ion concentration sensors are available for performing these measurements. One class of ion concentration sensors is based on ion sensitive transistors, such as the ion sensitive field effect transistor (ISFET). The ion sensitivity that is observed when the transistor is exposed to an electrolyte makes the ISFET a highly useful tool for pH sensors used in many fields, such as agriculture, environmental studies, and the food industry.

The ISFET is based on the structure of Metal-Oxide-Semiconductor (MOSFET). In an ISFET, the metal gate contact of the MOSFET is eliminated, exposing the gate insulator. The gate insulator can thus contact an electrolyte solution, when the ISFET is immersed in the solution. The ISFET sensing principle is based on charge absorption at the ion-solid interface between the sensing layer, which contains hydroxyl groups, and the electrolyte, from which hydroxyls may accept or donate protons. In this process, a double-layer capacitance is created with a potential drop which influences the threshold voltage of the transistor, so that the threshold drop corresponds to the ion concentration.

FIG. 1 shows a typical cross-section of an ISFET. Like a MOSFET, ISFET 100 contains reference electrode 110 which provides contact to the transistor gate, and two diffusion connections 120.1 and 120.2. ISFET 100 also has ion sensitive layer 130, which can contact the test solution.

The ISFET has an insulating layer applied on top of the gate structure, so the gate voltage is applied to a reference electrode. The ISFET threshold voltage is dependent on the interfaces between the reference electrode and the solution, and between the solution and the oxide on the gate. The flat-band voltage is therefore:

$$V_{FB} = E_{ref} - \Psi_0 + \chi_{sol} - \frac{\Phi_{Si}}{q} - \frac{Q_{ss} + Q_{ox}}{C_{ox}} \quad (1)$$

where $\Phi_{Si}$ is the silicon work-function, $Q_{ss}$ is the surface state density at the silicon surface, and $Q_{ox}$ is the fixed oxide charge, $E_{ref}$ is a constant related to the reference electrode potential, and $\chi_{sol}$ is the constant surface dipole potential of the solution. The surface potential $\Psi_0$ is created by chemical reactions between the hydroxyl groups with the surfaces of the oxide and the aqueous solution. During the chemical reactions, the hydroxyl sites bind or release hydrogen ions, creating a charge on the oxide surface that is opposite to the ion charge in the solution. In this way a double layer structure is created with capacitance $C_{dl}$ and a variable potential drop $\Psi_0$. Potential drop $\Psi_0$ operates as a serial voltage source to the gate electrode, and is linearly dependent on the hydrogen ion concentration in the solution (pH).

FIG. 2 shows the ISFET equivalent electrical circuit, containing FET 210, double layer capacitance $C_{dl}$ 220, and current source 230. Current source 230 represents the charge resulting from the potential drop To on the double layer capacitor. The ISFET's sensitivity is defined by the linear dependence $\Psi_0/pH$, and for high-performance sensors can reach up to 58 mV/pH.

Currently, ISFET-based ion concentration sensors require additional readout circuitry, in order to convert the ISFET electrical response to values corresponding to the ion concentration in the solution. The main reason for the use of a readout circuit is that pH fluctuations influence the threshold voltage, which is an internal FET parameter, and do not manifest themselves as a voltage signal at the output but rather as fluctuations of the transconductance. Transconductance is a passive parameter, so that deriving a voltage or current signal from the transconductance fluctuations requires attaching the sensor to conditioning and transmitting circuitry.

In order to obtain a measurement signal, the ISFET is associated with an analog interface circuit. When a constant drain-source voltage, $V_{ds}$, is applied, the ISFET itself converts the input voltage, $\Psi_0$, into a corresponding channel resistance, which manifests itself as a certain drain current, $I_D$. The ISFET response is described by P. Bergveld and A. Sibbald in "Analytical and Biomedical Applications of Ion-Selective Field Effect Transistors", Comprehensive Analytical Chemistry, vol. 12, 1988, which is hereby incorporated by reference. The readout circuit commonly couples the ISFET to devices such as operational amplifiers, current sources, and MOSFETs, which are combined in various feedback configurations. The readout circuit maintains the drain current and/or the drain-source voltage of the ISFET at a constant level.

Two examples of prior art ISFET readout interfaces are presented below. The configurations differ in structure, bias conditions, and the way the feedback signal is applied. These factors impact the complexity, performance (sensitivity, noise limits, etc.), and second-order effects (such as the body effect) of the readout circuit.

A first example of a prior-art readout circuit is the source-drain follower configuration shown in FIG. 3. The readout circuit is configured as an instrumental amplifier, and is realized with operational amplifiers A1, A2, and A3, with internal amplification equal to:

$$\left(\frac{r_{ds} + 2R_3}{r_{ds}}\right)\frac{R_5}{R_4}. \quad (2)$$

The ISFET operates in the linear region, with a constant drain-source voltage $V_{ds} = I_1 \cdot R_1$ for a constant $I_D$. The ISFET replaces a resistor within the instrumental amplifier configuration, so that the amplification factor varies in accordance with the properties of the ISFET. The change of the threshold voltage, $V_{th}$, is amplified at the $R_6$ output by:

$$\Delta V_{out} = \Delta V_{th} \cdot \left(\frac{R_6}{R_2}\right) \quad (3)$$

The ISFET source and drain connections are symmetrical, and have low resistance due to the internal feedback of amplifiers A1 and A2. The source-follower configuration is thus attractive for discrete implementations containing long wires.

The source-follower configuration is widely used in discrete implementations, but requires a large amount of hardware (four operational amplifiers and nine resistors), which makes it inapplicable for monolithic Microsystems with limited chip area. Note also that in monolithic implementations in CMOS technology the source-follower circuit is affected by the body effect of the n-channel ISFET. The source-drain follower readout circuit is therefore not suitable for monolithic Microsystems which are based on n-channel ISFETs, due to their low drift properties. This problem is not limited to the source-follower readout circuit, but occurs in many other configurations.

A second example of a readout circuit is the constant current driver shown in FIG. 4a. The constant current driver circuit uses the same principle as the source-drain follower, and can be integrated into discrete circuits or monolithic circuits with p-type ISFETs. The constant current driver configuration is discussed in P. Bergveld "Development of an Ion-Sensitive Solid-State Device for Neurophysiological Measurements", IEEE Trans. Biomedical Engineering, MBE-17, p. 70, 1970, and by S. Casans, D. Ramirez and A. E. Navarro in "Circuit Provides Constant Current for ISFETs/MEMFETs", EDN Access, Design Ideas, 2000, which are both hereby incorporated by reference. Current source $I_1$ produces a voltage drop across resistor $R_1$. The voltage follower reflects this voltage at the drain-source terminals of the ISFET as:

$$V_{ds} = I_1 \cdot R_1. \quad (4)$$

The drain current is kept constant via $I_2$. The ISFET works in linear region. $V_{out}$, with:

$$V_{out} = -V_{th}(ISFET) - \frac{I_2}{\beta \cdot I_1 \cdot R_1} - \frac{I_1 \cdot R_1}{2} \quad (5)$$

Although, the structure of constant current driver readout circuit is somewhat simplified, it still suffers from the body effect in n-type ISFET, and thus is unsuitable for application in CMOS microsystems.

Another example of a readout circuit is the ISFET/MOSFET differential pair configuration shown in FIG. 4b. The readout circuit is based on the integration of an ISFET and a MOSFET in a differential amplifier circuit, with voltage feedback of the output signal to the MOSFET gate, a concept known as indirect feedback. The ISFET drain current is thus kept constant, to compensate for the solid-state temperature sensitivity without using a differential ISFET configuration.

The amplification of the ISFET/MOSFET Differential Pair circuit is:

$$\frac{\partial V_{out}}{\partial \Psi_0} = \frac{A}{A+1} \quad (6)$$

Thermally induced changes in the ISFET and MOSFET drain currents are rejected by the differential input stage as a common mode signal. However, the ISFET body effect makes the ISFET/MOSFET differential pair configuration problematic for implementation in CMOS Microsystems.

An additional example of a readout circuit is the source follower configuration for discrete systems shown in FIG. 4c. This configuration is described by C. G. Jakobson and Y. Nemirovsky, in "1/f Noise in Ion Sensitive Field Effect Transistors from Subthreshold to Saturation", in IEEE Trans. on Electron Devices, vol. 46, pp. 259-261, 1999, which is hereby incorporated by reference. The readout circuit implements the principle of source follower for discrete applications, while eliminating the voltage drop on connecting wires by using operational amplifiers as shown in FIG. 4c.

Readout circuit operation is based on the following relationships:

$$I_D = V_{REF}/(R_1 + R_2) \quad (7)$$

$$V_{OUT} = V_{DS} = V_{GS}(\text{pH}) \quad (8)$$

The discrete system source follower allows simultaneous measurement of n-channel and p-channel ISFET sensors, while maintaining a constant drain current. Changes in $V_T$ due to a changing pH manifest themselves in changes in $I_D$, causing an increase in $V_{OUT}$ which returns the current to initial value.

The loop transmission of the circuit is:

$$LT = A_V g_m \cdot R \quad (9)$$

so that the stability of the circuit can be controlled by the value of R. The capacitor, C, is added for zero-pole compensation.

Body effect considerations affect the use of this configuration in CMOS monolithic microsystems. When the feedback signal returns to the source, the signal causes a $|V_{BS}|>0$ in the n-channel ISFET, resulting in an additional increase in $V_T$ that is not due to the pH value. The $V_T$ increase is applied once again to the amplifier stage, and results in restrained oscillations leading to a final incorrect value which is larger than the desired result.

Other readout circuits are found in the prior art, but all require adding additional components to the ISFET in order to obtain a voltage which accurately reflects the ion concentration of the sensed environment. Although the existing readout techniques are widely used in discrete system applications, only a few interfaces are suitable for integration in a microsystem in CMOS technology due to body effect concerns. N-channel ISFETs are generally used in CMOS-based integrations, due to low drift properties, with the p-type substrate globally and constantly grounded. Grounding the p-type substrate limits the possibilities of source biasing in ISFET. None of the prior-art techniques supplies a full assembly of high-performance features, such as constant values of $I_d$ and/or $V_{ds}$, body effect elimination, low temperature sensitivity, and design simplicity.

The disadvantages of current transistor-based ion concentration sensors with readout circuits are numerous, and include large area, higher power consumption, more bandwidth and stability limitations, and increased design complexity. Solving these problems could have potential uses for numerous fields, including biomedical applications, such as array-type monitoring in biotelemetry and miniaturized clinical applications.

There is thus a widely recognized need for, and it would be highly advantageous to have, an ion concentration sensor devoid of the above limitations.

SUMMARY OF THE INVENTION

According to a first aspect of the present invention there is provided an ion concentration sensor which produces a signal reflective of the ion concentration within a solution. The ion concentration sensor is based on an ion sensitive transistor having a solution input, a reference input, a diffusion input, and a diffusion output. The ion sensitive transistor is connected as a pass transistor, such that the diffusion output provides an electrical signal indicating an ion concentration in a solution contacting the solution input.

Preferably, the ion concentration sensor also contains a threshold drop tracker connected between the diffusion input and the diffusion output, for obtaining the electrical signal as a voltage drop between the diffusion input and the diffusion output.

Preferably, the ion concentration sensor also contains an ion concentration calculator, for calculating the ion concentration from a voltage drop between the diffusion input and the diffusion output.

Preferably, the ion is a hydrogen ion.

Preferably, the ion sensitive transistor is an ion sensitive field effect transistor (ISFET).

Preferably, the ion sensitive transistor is a p-type transistor.

Preferably, the ion sensitive transistor is an n-type transistor.

Preferably, the ion concentration sensor also contains a pulse source, for applying a pulsed signal to the diffusion input.

Preferably, the pulse source is a square wave generator.

Preferably, the ion concentration sensor also contains an envelope generator for providing an envelope of the electrical signal.

Preferably, the envelope generator is a low pass filter (LPF).

Preferably, the frequency of the pulsed signal is greater than twice the maximum frequency of the rate of change of the ion concentration.

Preferably, the ion concentration sensor also contains a data source, for modulating the pulsed signal with digital data.

Preferably, the ion concentration sensor also contains a digitizer, for converting the electrical signal to digital format.

Preferably, the ion concentration sensor also contains a sweep generator, for applying a sequence of positive and negative voltage sweeps to the reference input.

Preferably, the ion concentration sensor also contains a voltage source, for applying a stable reference voltage to the reference input.

Preferably, the ion concentration sensor also contains an error eliminator. The error eliminator consists of an error detector, which provides an error signal essentially equal to a body effect of the ion sensitive transistor, and a subtractor, which subtracts the error signal from the electrical signal.

Preferably, the error detector consists of a reference transistor having a second reference input, a second diffusion input, and a second diffusion output, the reference transistor being configured as a pass transistor and connected in parallel with the ion sensitive transistor.

Preferably, the reference transistor is a reference field effect transistor (REFET).

According to a second aspect of the present invention there is provided a dual-mode sensor, for simultaneous measurement of the intensity of a light and the concentration of an ion in a solution. The dual-mode sensor consists of a light sensitive device, which has a discharge rate indicative of the light intensity, and an ion sensitive transistor configured as a pass transistor. The ion sensitive transistor has a solution input, a reference input, a diffusion input, and a diffusion output. The diffusion output of the ion sensitive transistor and the output of the light sensitive device are connected together, to form the sensor output. The sensor output provides an electrical signal indicating the intensity of a light and of an ion concentration in the solution.

Preferably, the ion sensitive transistor is an ISFET.

Preferably, the ion sensitive transistor is an n-type transistor.

Preferably, the ion sensitive transistor is a p-type transistor.

Preferably, the light sensitive device is a photodiode.

Preferably, the dual-mode sensor also contains an amplifier associated with the sensor output, for amplifying the electrical signal.

Preferably, the dual-mode sensor also contains a switch associated with the amplifier, for connecting and disconnecting the sensor output in accordance with a control signal.

Preferably, the dual-mode sensor also contains an envelope generator associated with the sensor output, for providing an envelope of the electrical signal.

Preferably, the dual-mode sensor also contains a threshold drop tracker connected between the diffusion input and the diffusion output, for obtaining the electrical signal as a voltage drop between the diffusion input and the diffusion output.

Preferably, the dual-mode sensor also contains a slope measurer associated with the sensor output, for determining a rate of change of the electrical signal.

Preferably, the dual-mode sensor also contains a fall detector associated with the sensor output, for determining an amplitude drop of the electrical signal over a single cycle.

Preferably, the dual-mode sensor is incorporated within a biomedical sensor.

Preferably, the biomedical sensor is constructed for use in a gastro-intestinal environment, for measuring X-ray intensity and pH (potential of Hydrogen) within a digestive tract.

Preferably, the biomedical sensor is a sperm mobility measurer, consisting of an image analyzer and a correlator. The image analyzer analyzes a sequence of images of a sperm sample to identify sperm motion. The correlator correlates the sperm motion with the pH measurement.

Preferably, the biomedical sensor is a cell identification device, for identifying cells within a sample in accordance with a fluoroscopic tag associated with the cell and the pH of the sample.

According to a third aspect of the present invention there is provided a test device for performing ion concentration and image analysis of a sample. The test device consists of at least one dual-mode sensor, an ion concentration analyzer, an image analyzer, and a correlator. Each of the dual-mode sensors consists of a light sensitive device, which has a discharge rate indicative of the light intensity, and an ion sensitive transistor configured as a pass transistor. The ion sensitive transistor has a solution input, a reference input, a diffusion input, and a diffusion output. The diffusion output of the ion sensitive transistor and the output of the light sensitive device are connected together, to form the sensor output. The sensor output provides an electrical signal indicating the intensity of a light and of an ion concentration in the solution. The ion concentration analyzer analyzes ion concentration data obtained from the dual-mode sensors. The image analyzer analyzes optical data obtained from the dual-mode sensors. The correlator correlates the analyzed ion concentrations with the analyzed images.

Preferably, the test device has digital signal processing (DSP) functionality.

Preferably, the correlator also correlates the analyzed ion concentrations and the analyzed images with externally provided data.

Preferably, the externally provided data is optical data.

According to a fourth aspect of the present invention there is provided a sensor array consisting of an array of dual-mode sensors. Each of the dual-mode sensors consists of a light sensitive device, which has a discharge rate indicative of the light intensity, and an ion sensitive transistor configured as a pass transistor. The ion sensitive transistor has a solution input, a reference input, a diffusion input, and a diffusion output. The diffusion output of the ion sensitive transistor and the output of the light sensitive device are connected together, to form the sensor output. The sensor output provides an electrical signal indicating the intensity of a light and of an ion concentration in the solution.

Preferably, each of the dual mode sensors has a switch, for connecting and disconnecting the sensor output in accordance with a control signal.

Preferably, the sensor array also contains a switching device for controlling the switches.

According to a fifth aspect of the present invention there is provided a sensor array consisting of an array of ion concentration sensors. Each of the concentration sensors consists of an ion sensitive transistor having a solution input, a reference input, a diffusion input, and a diffusion output. The ion sensitive transistor is connected as a pass transistor, such that the diffusion output provides an electrical signal indicating an ion concentration in a solution contacting the solution input.

According to a sixth aspect of the present invention there is provided a method for producing a signal reflective of the ion concentration within a solution, utilizing an ion sensitive transistor having a first ion sensitive portion, a first reference input, a first diffusion input, and a first diffusion output. The method consists of configuring the ion sensitive transistor as a pass transistor, applying the solution to the first ion sensitive portion, and obtaining an electrical signal indicating an ion concentration in the solution from a voltage drop between the first diffusion input and the first diffusion output.

Preferably, configuring the ion sensitive transistor consists of providing a reference voltage to the first reference input, and inputting a baseline signal to the first diffusion input.

Preferably, the ion is a hydrogen ion.

Preferably, the ion sensitive transistor is an ISFET.

Preferably, the method contains the further step of generating an envelope of a signal at the diffusion output.

Preferably, the baseline signal is a pulsed signal.

Preferably, the method contains the further step of modulating the pulsed signal with digital data.

Preferably, the frequency of the pulsed signal is set to be greater than twice a maximum frequency of a rate of change of the ion concentration.

Preferably, the level of the reference voltage is essentially stable.

Preferably, the method contains the further step of applying a sequence of positive and negative sweeps to the reference input.

Preferably, the method contains the further steps of configuring a reference transistor having a second reference input, a second diffusion input, and a second diffusion output as a pass transistor, in parallel with the ion sensitive transistor, and subtracting the error signal at the second diffusion output from the electrical signal.

Preferably, configuring the reference transistor consists of providing the reference voltage to the second reference input and inputting the baseline signal to the second diffusion input.

According to a seventh aspect of the present invention there is provided a method for producing a signal simultaneously reflective of the intensity of a light and of the concentration of ions within a solution. First, an ion sensitive transistor, having an ion sensitive portion, a reference input, a diffusion input, and a diffusion output, is configured as a pass transistor. The diffusion output is then connected to a light sensitive device having a discharge rate indicative of the light intensity, and the solution is applied to the ion sensitive portion. Finally, an electrical signal indicating the intensity of a light and of an ion concentration in the solution is obtained from the voltage drop between the diffusion input and the diffusion output.

Preferably, configuring the ion sensitive transistor consists of providing a reference voltage to the reference input, and inputting a pulsed signal to the diffusion input.

Preferably, the ion sensitive transistor is an ISFET.

Preferably, the method contains the further step of isolating the light-responsive component of the electrical signal.

Preferably, the rate of change of the output signal encodes the light intensity.

Preferably, the amplitude drop of the output signal over a single cycle encodes the light intensity.

Preferably, the light sensitive device is a photodiode.

According to an eighth aspect of the present invention there is provided a method for performing ion concentration and image analysis of a sample, from ion concentration and image data provided by at least one dual-mode sensor. Each of the dual-mode sensors consists of a light sensitive device, which has a discharge rate indicative of the light intensity, and an ion sensitive transistor configured as a pass transistor. The ion sensitive transistor has a solution input, a reference input, a diffusion input, and a diffusion output. The diffusion output of the ion sensitive transistor and the output of the light sensitive device are connected together, to form the sensor output. The sensor output provides an electrical signal indicating the intensity of a light and of an ion concentration in the solution. The method consists of analyzing the ion concentration data, analyzing the image data, and correlating the analyzed ion concentrations with the analyzed images.

Preferably, the method contains the further step of correlating the analyzed ion concentration and image data with externally provided data.

Preferably, the externally provided data is optical data.

The present invention successfully addresses the shortcomings of the presently known configurations by providing an ion concentration sensor based on an ion sensitive transistor which is configured as a pass transistor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows the typical cross-section of an ISFET.

FIG. 2 shows the equivalent electronic circuit of an ISFET.

FIG. 3 is a circuit diagram of a example of a prior-art source-drain follower readout circuit.

FIG. 4a is a circuit diagram of a constant current driver readout circuit.

FIG. 4b is a circuit diagram of an ISFET/MOSFET differential pair readout circuit.

FIG. 4c is a circuit diagram of a source follower readout circuit for discrete systems.

FIG. 5 is a simplified block diagram of a first ion concentration sensor, according to a preferred embodiment of the present invention.

FIG. 6 is a simplified block diagram of a second ion concentration sensor, according to a preferred embodiment of the present invention.

FIG. 7 illustrates the response of an ion concentration sensor to a square wave baseline signal.

FIG. 8 is a simplified block diagram of an ion concentration sensor with a pulsed baseline input signal, according to a preferred embodiment of the present invention.

FIG. 9 shows the typical spectral power density of ISFET 1/f noise.

Figure 10:
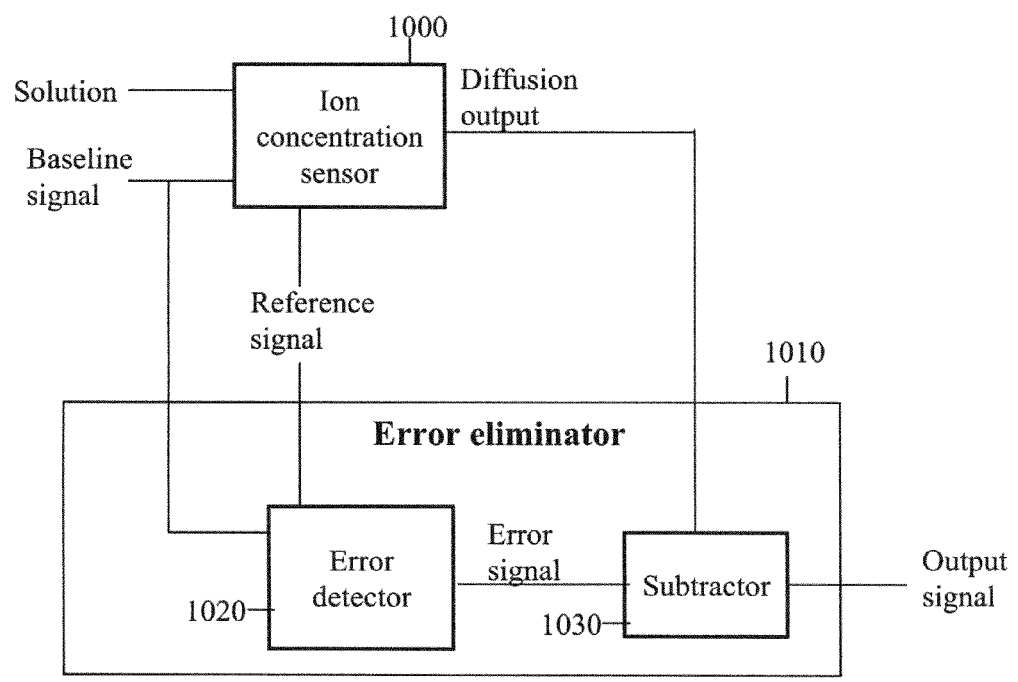

FIG. 10 is a simplified block diagram of an ion concentration sensor with error compensation, according to a preferred embodiment of the present invention.

Figure 11:
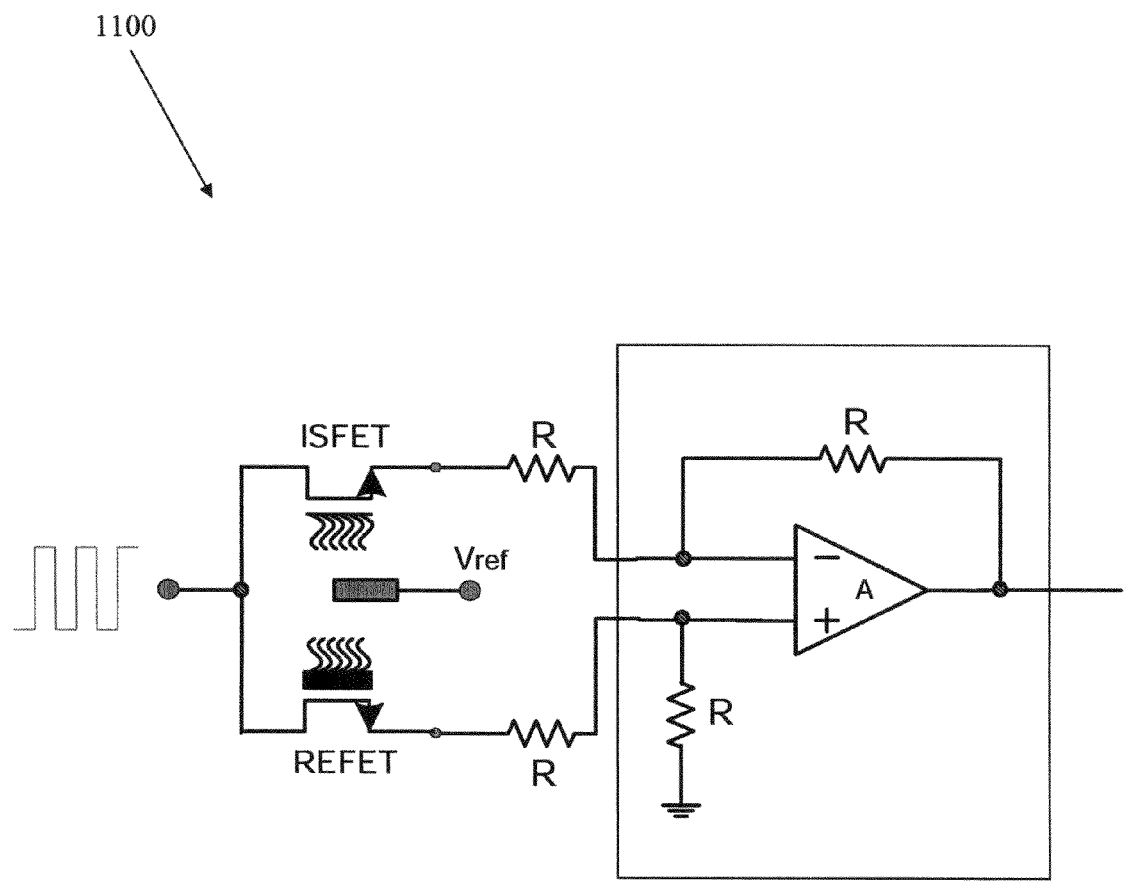

FIG. 11 is a simplified circuit diagram of an ion concentration sensor with a REFET-based error eliminator, according to a preferred embodiment of the present invention.

Figure 12:
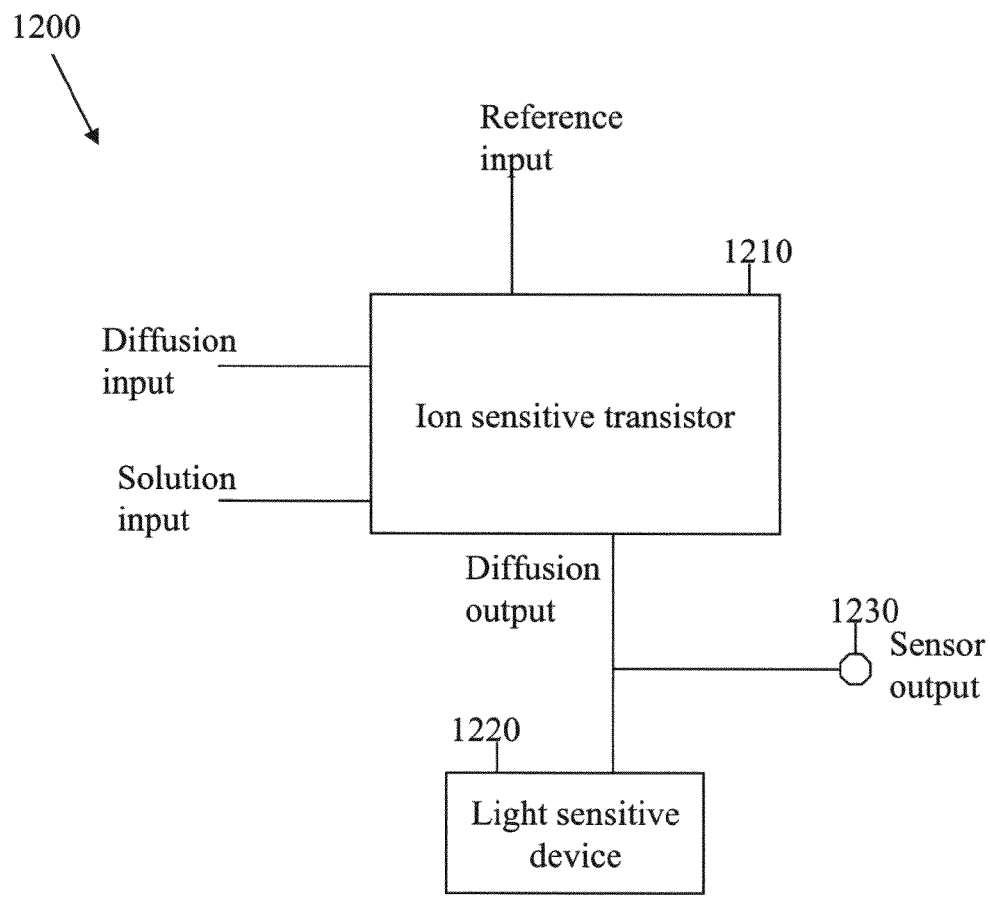

FIG. 12 is a simplified block diagram of a first dual-mode sensor, according to a preferred embodiment of the present invention.

Figure 13A:
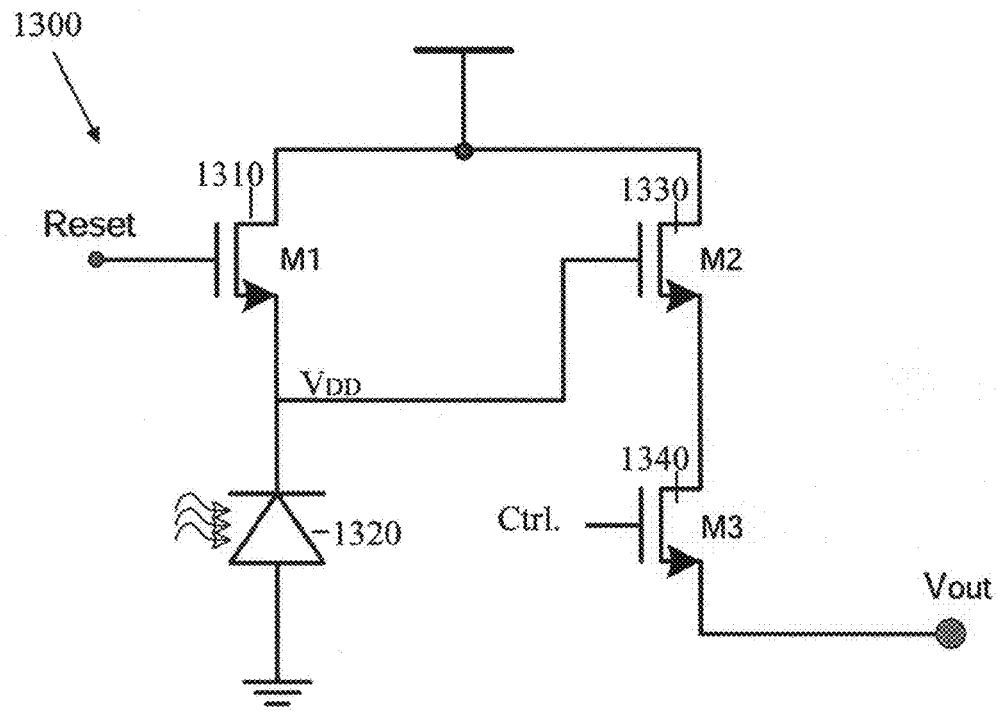
Figure 13B:
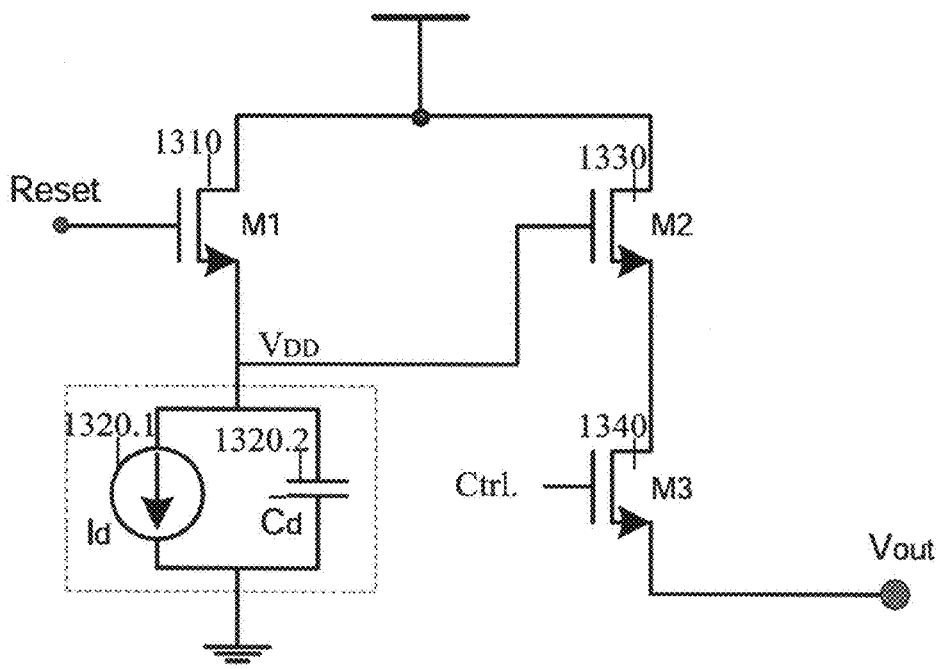

FIGS. 13a and 13b are a simplified circuit diagram and equivalent circuit of a prior art Active Pixel Sensor.

Figure 14:
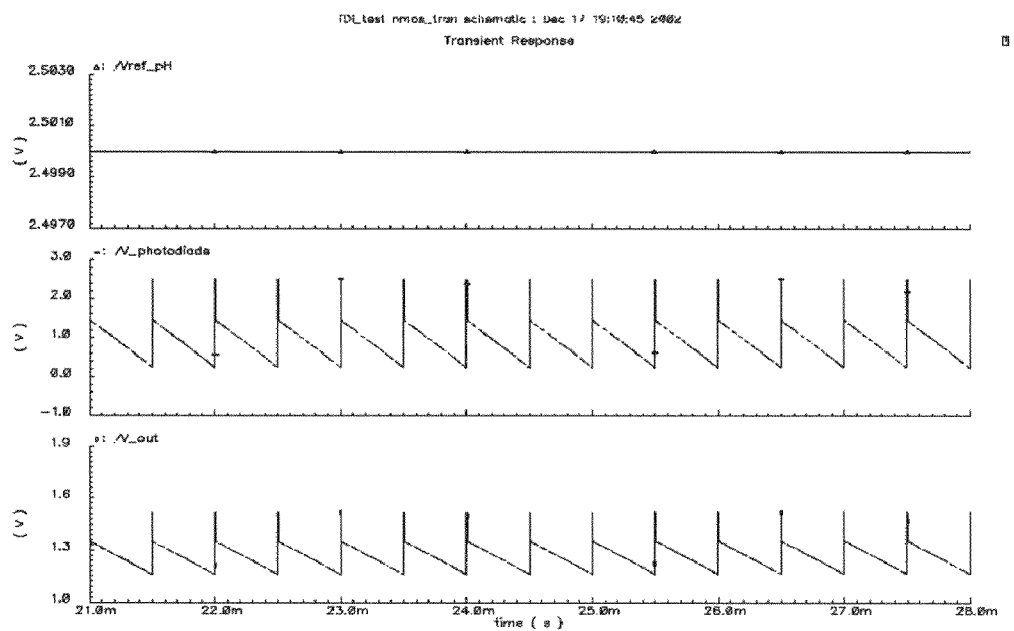

FIG. 14 presents simulation results of a standard APS sensor under constant illumination.

Figure 15:
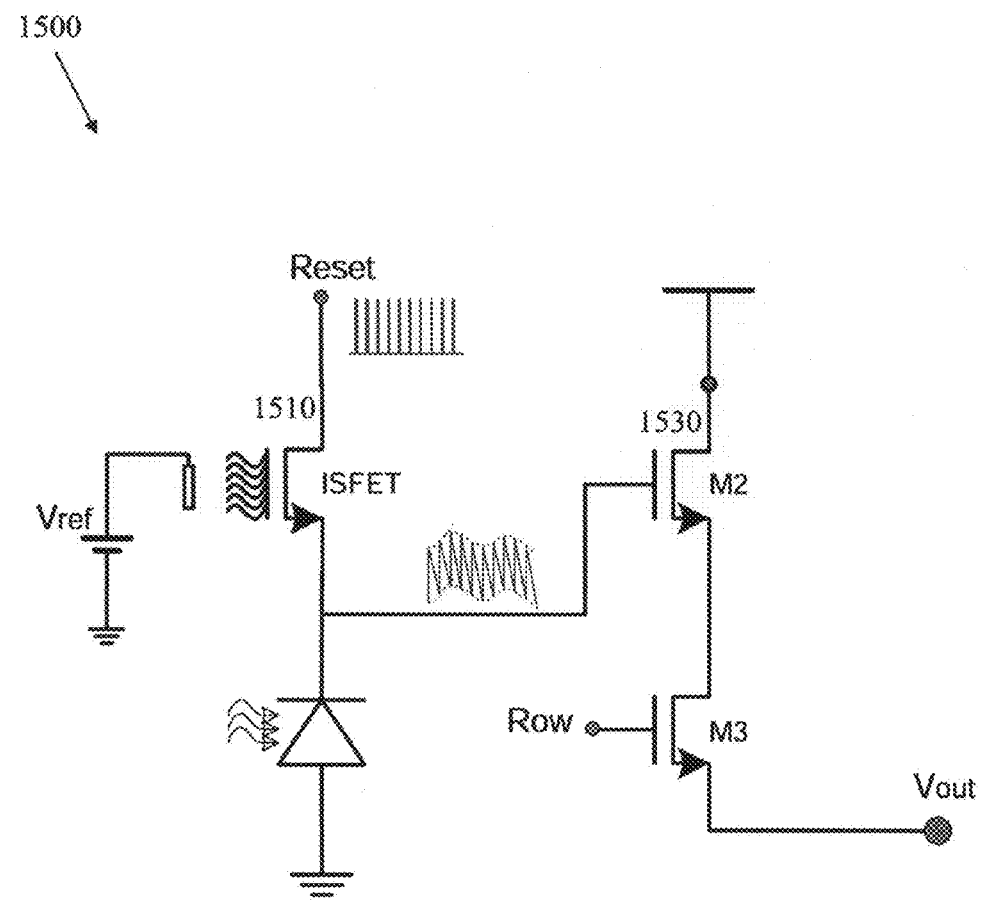

FIG. 15 is a simplified circuit diagram of a dual-mode sensor having an ISFET-based ion concentration sensor, according to a preferred embodiment of the present invention.

Figure 16A:
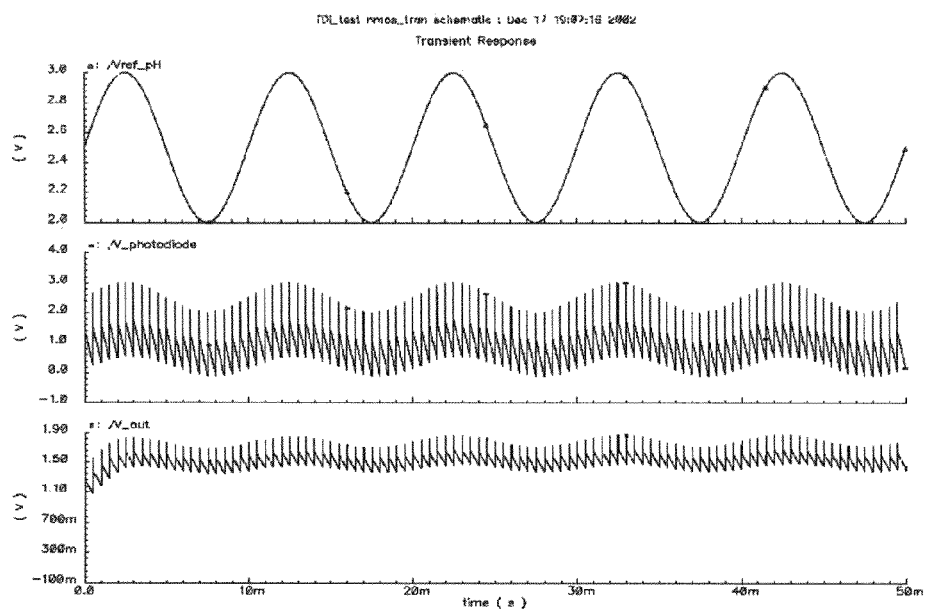
Figure 16B:
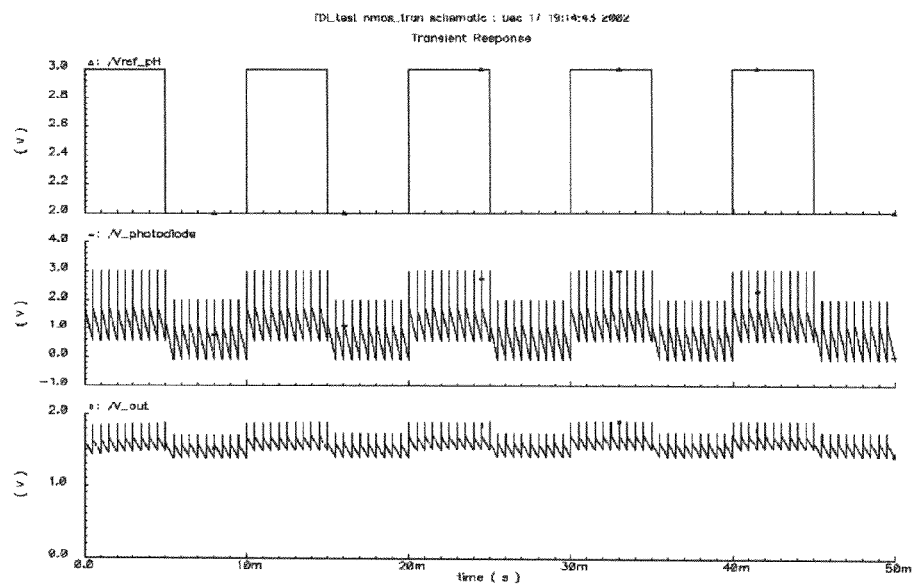

FIGS. 16a and 16b show the simulated response of an ISFET-based dual-mode sensor to pH fluctuations, under conditions of constant illumination.

Figure 17:
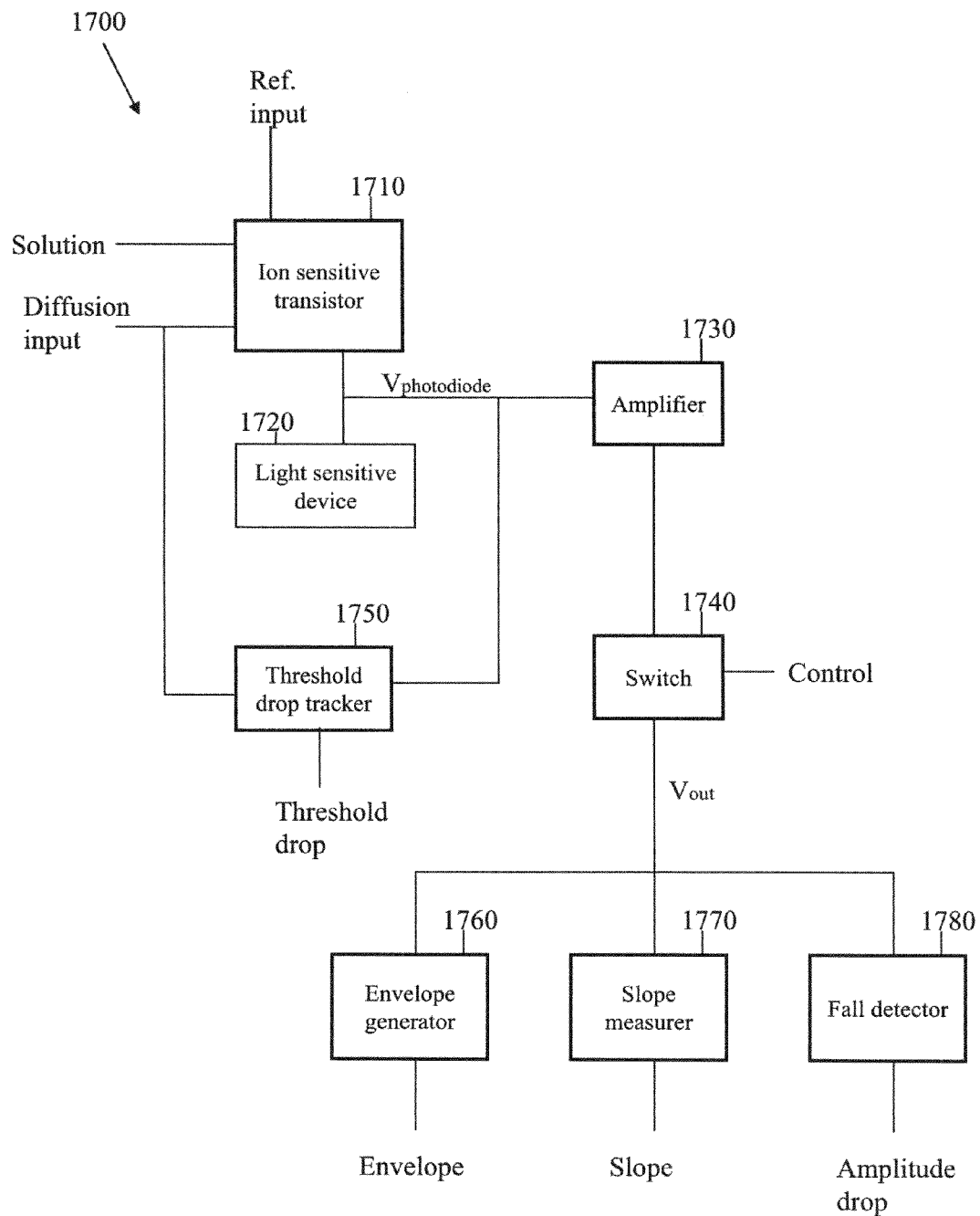

FIG. 17 is a simplified block diagram of a second dual mode sensor, according to a second preferred embodiment of the present invention.

Figure 18:
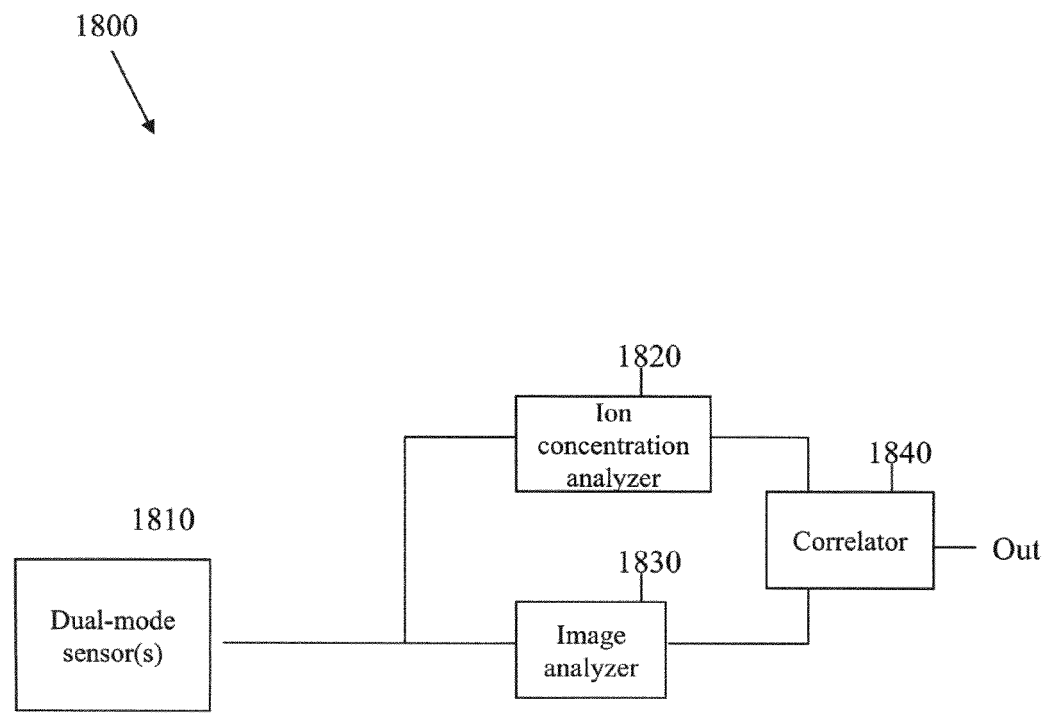

FIG. 18 is a simplified block diagram of a test device for performing ion concentration and image analysis of a sample, according to a preferred embodiment of the present invention.

Figure 19:
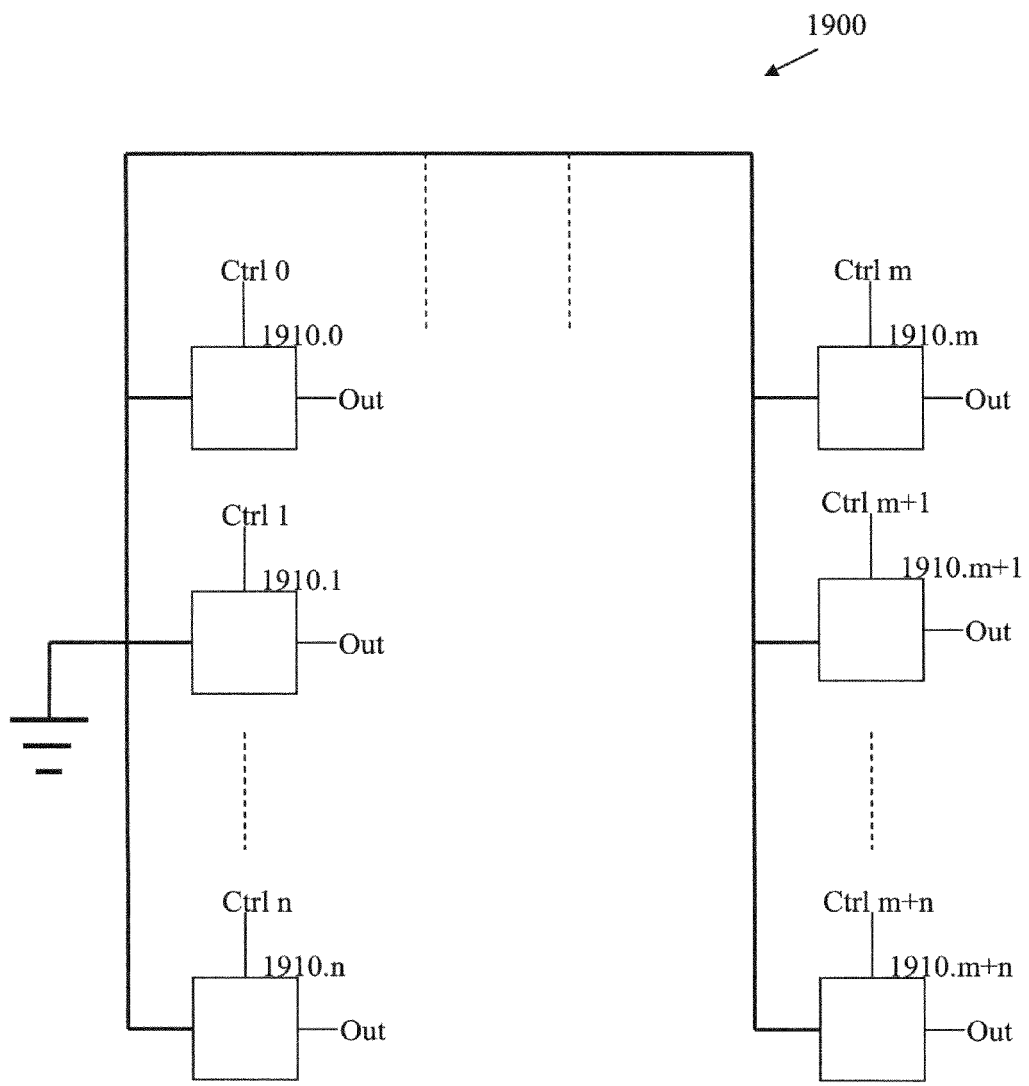

FIG. 19 is a simplified block diagram of a sensor array, in accordance with a preferred embodiment of the present invention.

Figure 20:
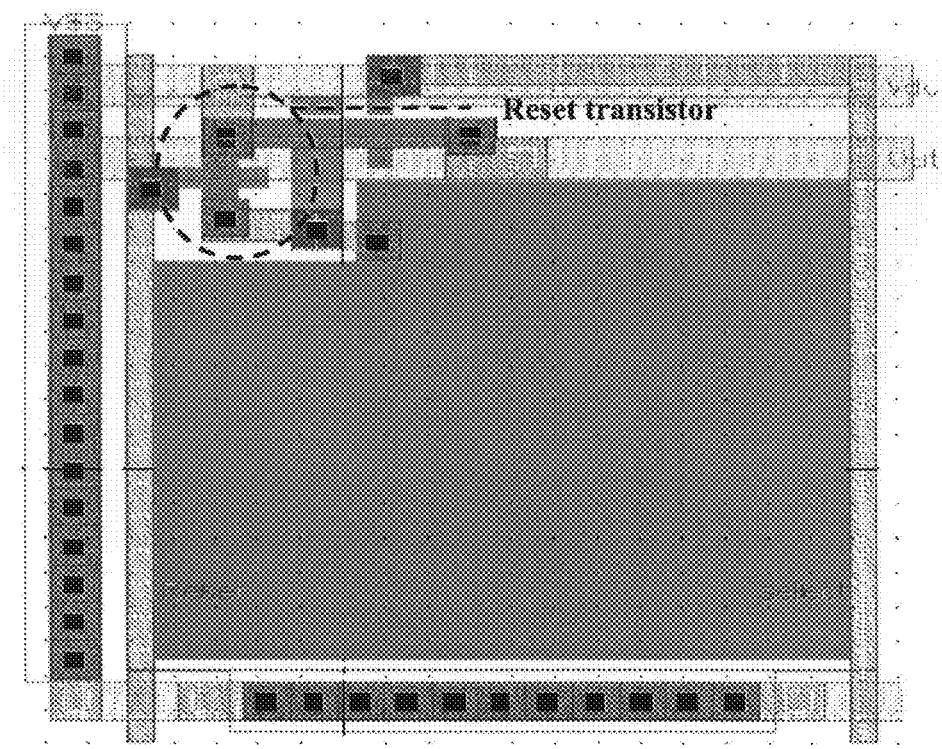

FIG. 20 shows the layout of a 10×10 μm APS pixel in 0.35 μm CMOS technology

Figure 21:
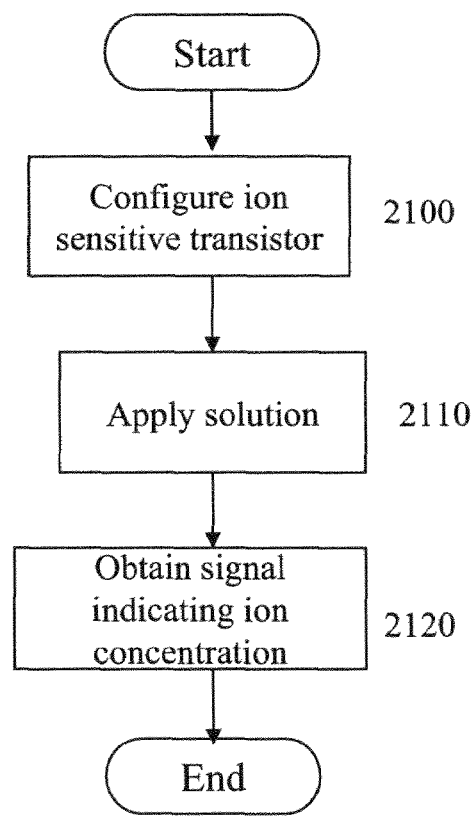

FIG. 21 is a simplified flowchart of a method for producing a signal reflective of the ion concentration within a solution, according to a preferred embodiment of the present invention.

Figure 22:
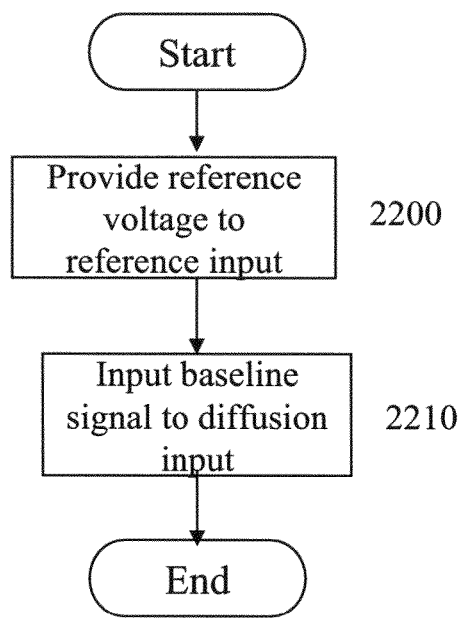

FIG. 22 is a simplified flowchart of a method for configuring an ion sensitive transistor, according to a preferred embodiment of the present invention.

Figure 23:
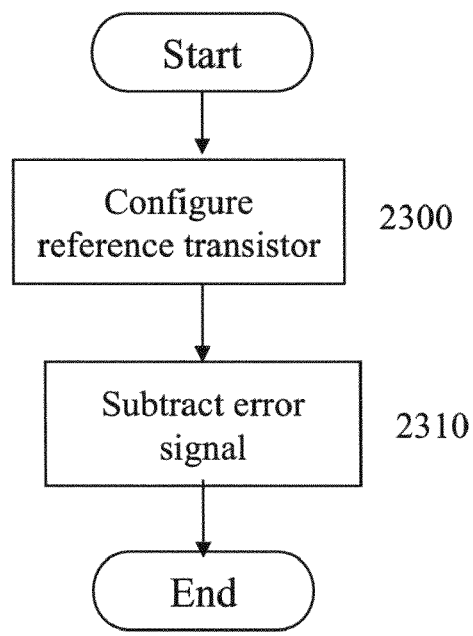

FIG. 23 is a simplified flowchart of a method for error elimination, according to a preferred embodiment of the present invention.

Figure 24:
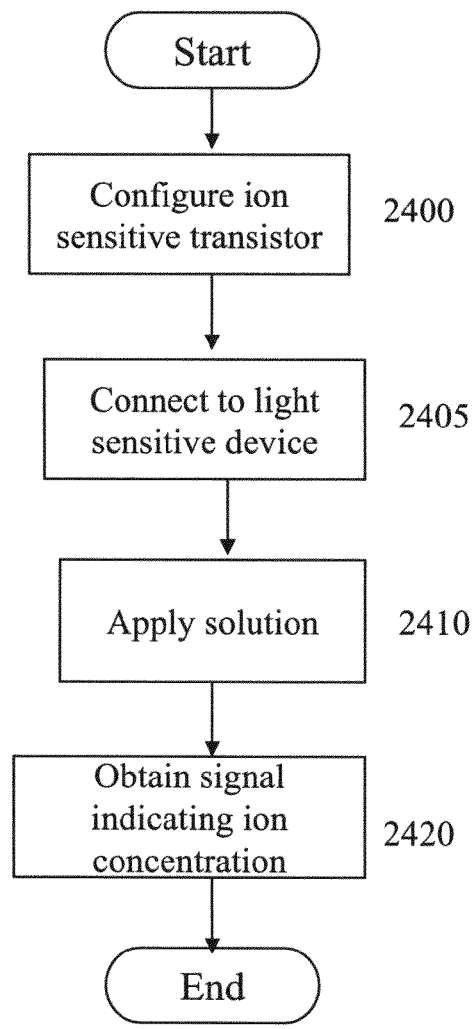

FIG. 24 is a simplified flowchart of a method for producing a signal simultaneously reflective of the intensity of a light and of the concentration of ions within a solution, according to a preferred embodiment of the present invention.

Figure 25:
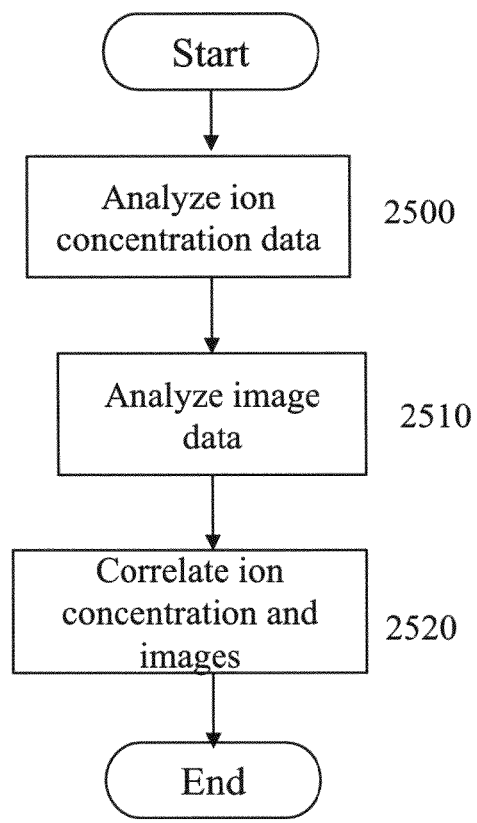

FIG. 25 is a simplified flowchart of a method for performing ion concentration and image analysis of a sample, according to a preferred embodiment of the present invention.

Figure 26:
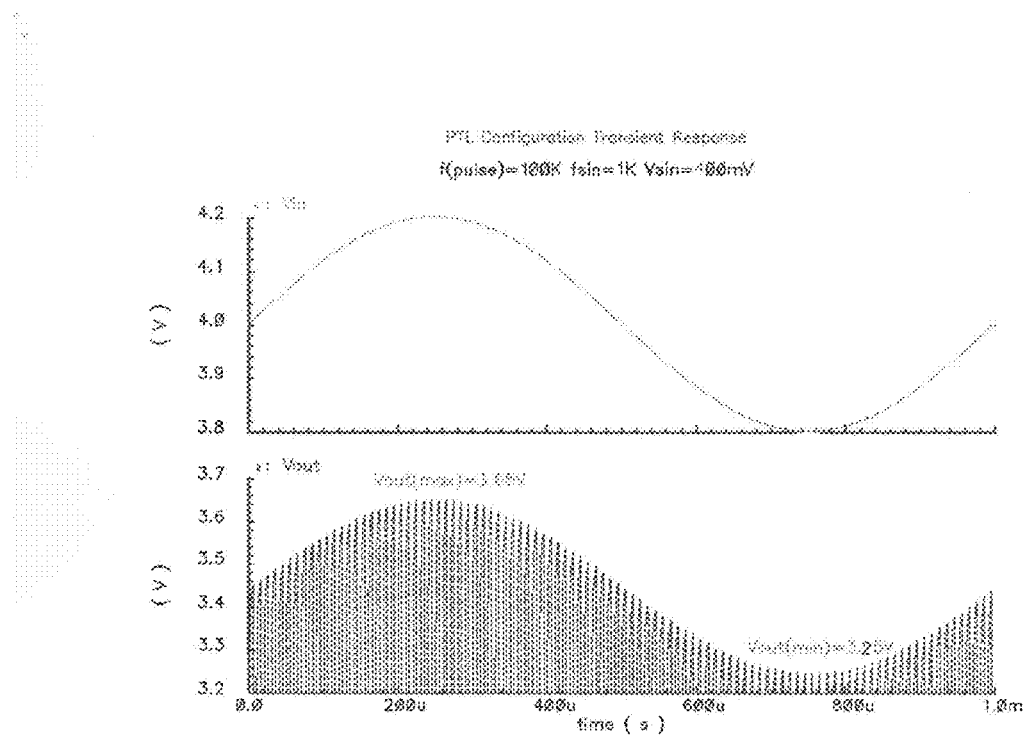

FIG. 26 shows simulation results of the transient response of an ISFET-based ion concentration sensor to a 400 mVp-p sinusoidal input.

Figure 27:
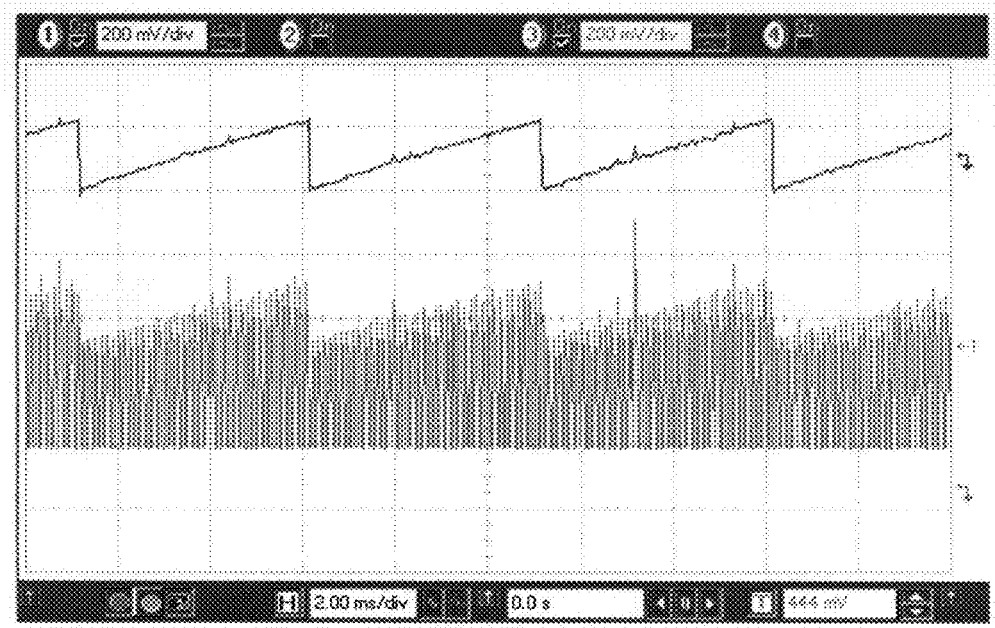

FIG. 27 shows a measured response of an ISFET-based ion concentration sensor to a triangular signal.

Figure 28:
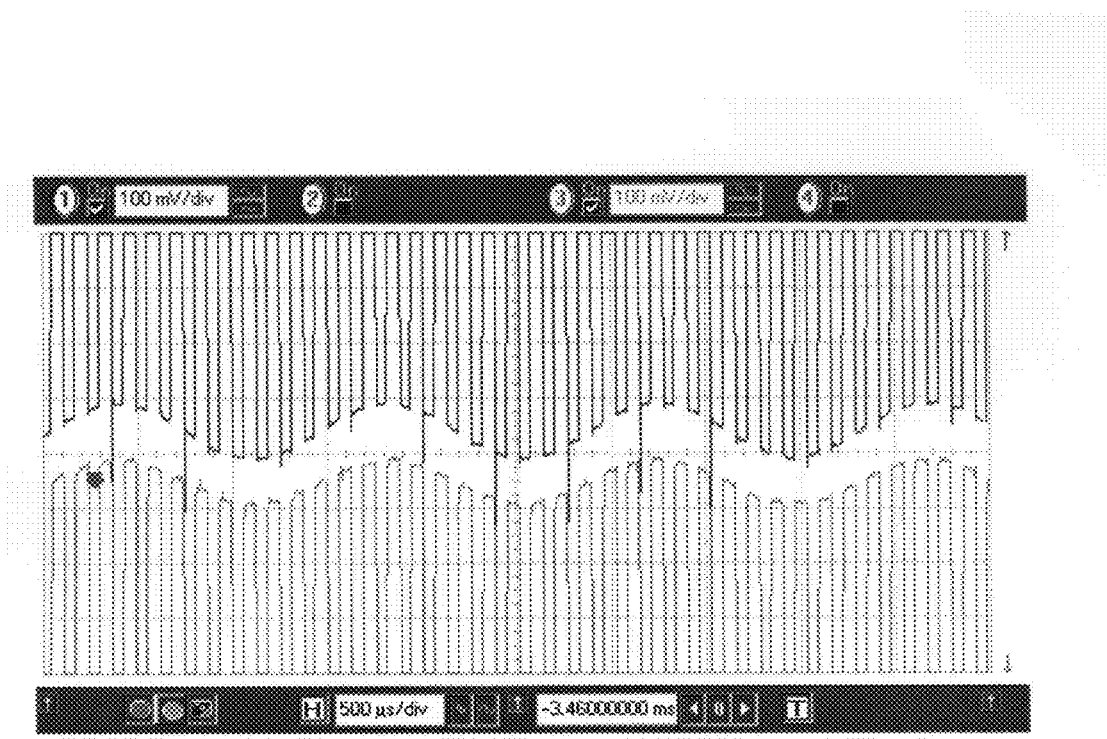

FIG. 28 shows the response of an ISFET-based ion concentration sensor to a sinusoidal signal.

Figure 29A:
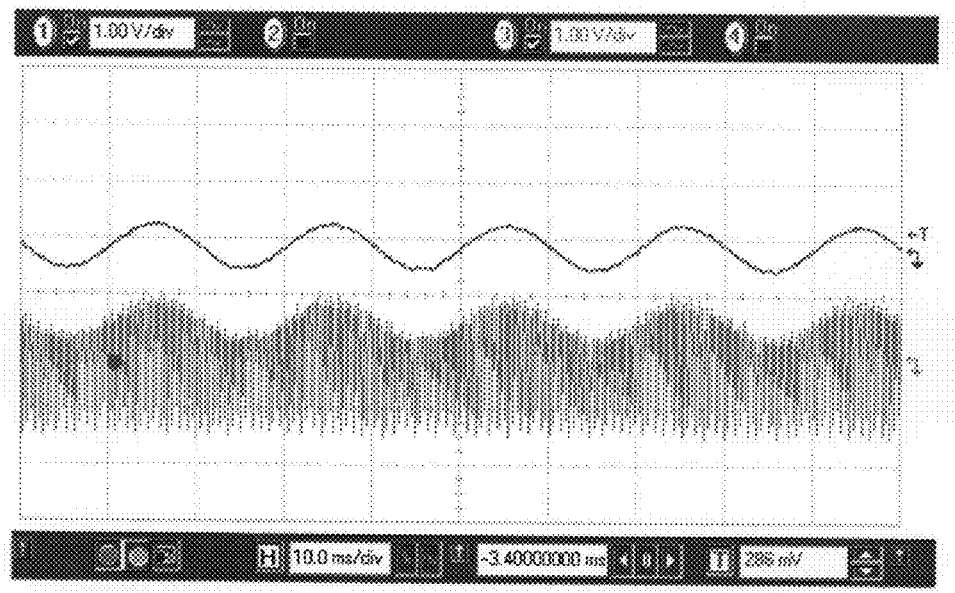
Figure 29B:
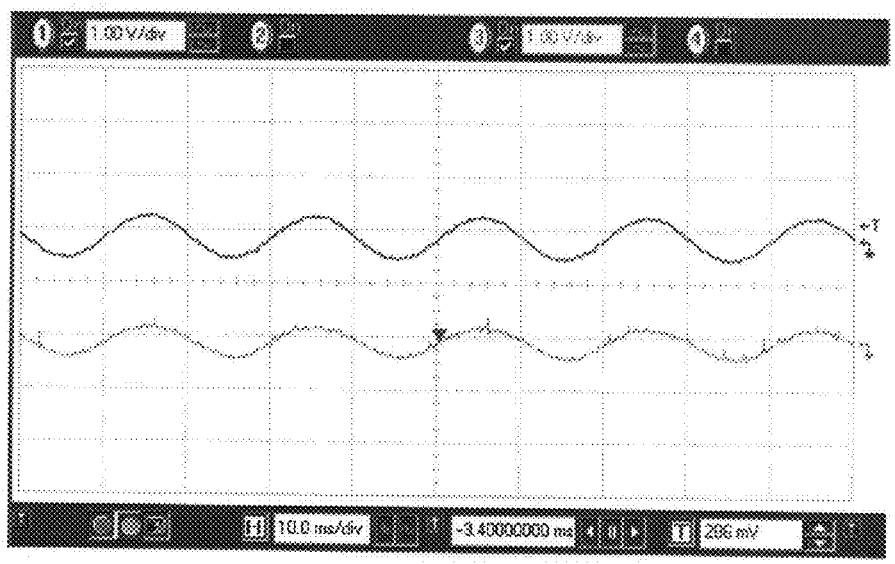

FIGS. 29a and 29b show the pass-transistor response to a sinusoidal input, before and after filtering by an LPF.

Figure 30A:
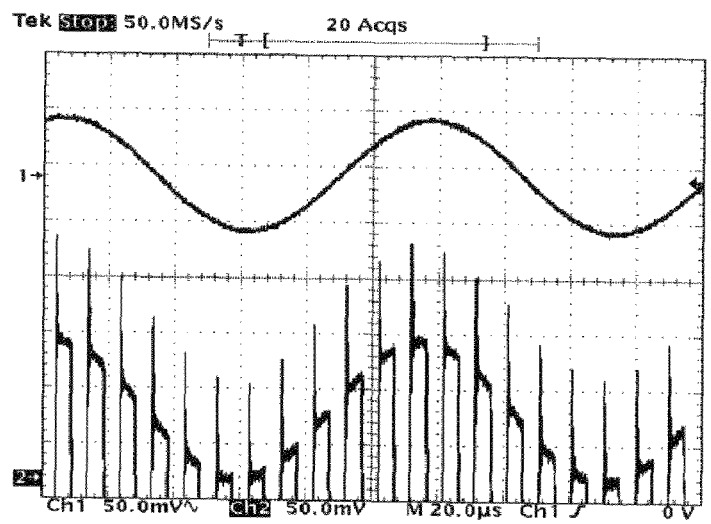
Figure 30B:
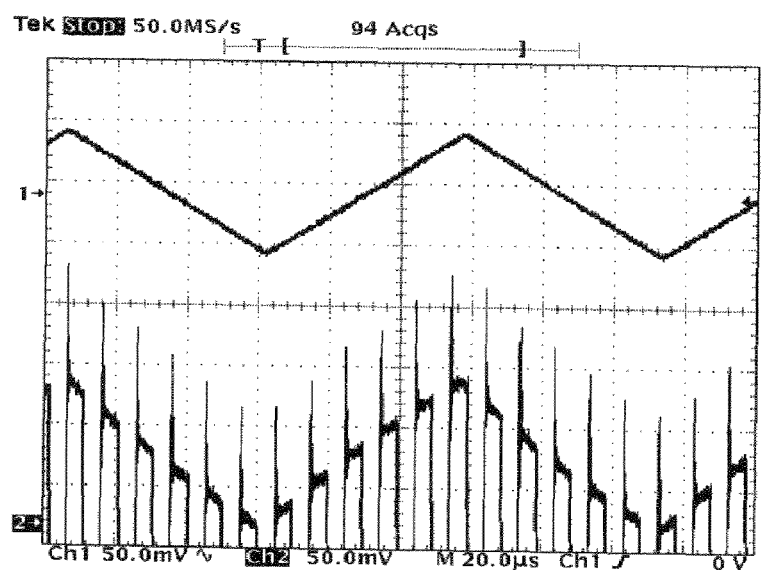

FIGS. 30a and 30b show the response of an ion concentration sensor sampling a sinusoidal and triangular signal respectively.

DESCRIPTION OF THE PREFERRED EMBODIMENTS

The present embodiments are of an ion concentration sensor, which does not require readout circuitry. Specifically, the present embodiments use the voltage threshold drop of an ion sensitive transistor configured as a pass transistor to determine the ion concentration of a solution.

In the present embodiments, an ion sensitive transistor is configured as a pass transistor in order to act as an ion concentration sensor, without requiring additional readout circuitry. The pass transistor configuration is based on standard pass transistor logic (PTL), which applies a control signal to the gate of an n-type transistor, in particular to an n-type MOSFET, as described by N. H. E. Weste and K. Eshraghian in "Principles of CMOS VLSI Design", pp. 51-57, 1993, which is hereby incorporated by reference. An additional input signal is applied to a MOSFET diffusion connection. The input signal is transferred through the MOSFET according to the value of the control signal. PTL circuits are much simpler than standard CMOS implementations, but have an important drawback for logic signals. When the signal transmitted through the pass gate is high, a voltage drop occurs at the output, so that the value of the output signal is lower than the input signal. This drop, denoted the threshold drop or $V_T$, is because the potential difference between the gate and the source of the FET must be higher than $V_T$ to allow current conduction. Once the output node is charged to a high enough value and the voltage across the FET equalizes to $V_T$, the current flow is stopped. Output charging stops as well, leaving a $V_T$ drop at the diffusion output.

In the present embodiments of an ion concentration sensor the voltage threshold drop becomes a valuable property, since in the pass-transistor configuration the threshold drop reflects the ion concentration as will be explained in greater detail below. The ion concentration can thus be detected from the threshold drop, eliminating the need for conditioning and transmitting circuitry within the sensor.

The principles and operation of an ion concentration sensor according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
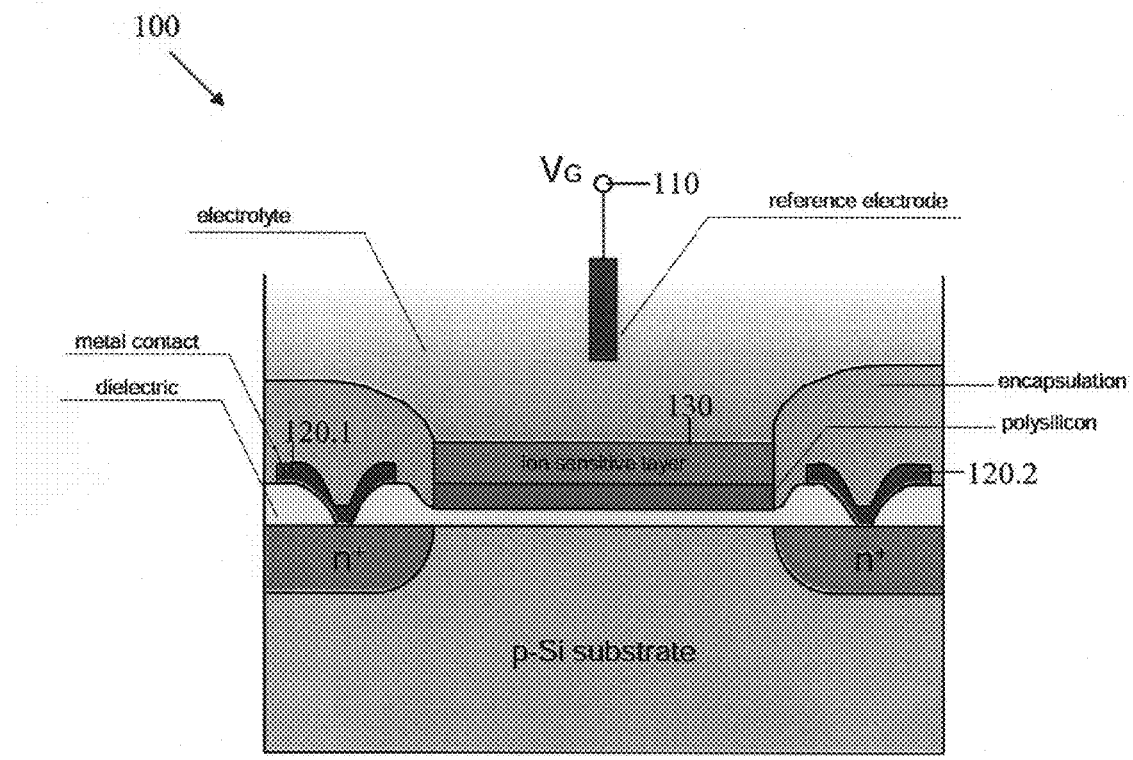
Figure 2:
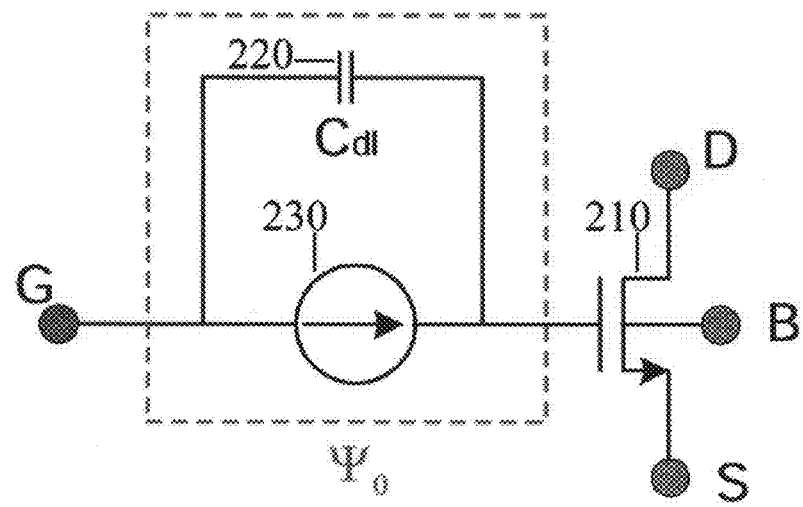
Figure 5:
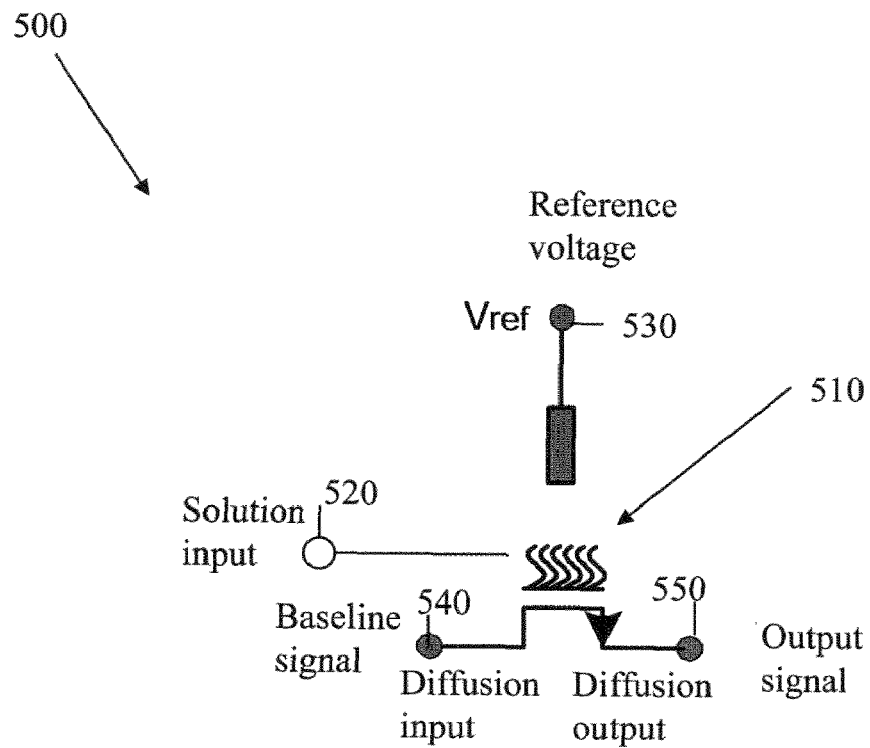

Reference is now made to FIG. 5, which is a simplified block diagram of a first ion concentration sensor, according to a preferred embodiment of the present invention. Ion concentration sensor 500 consists of ion sensitive transistor 510, which is connected as a pass transistor as described below. Ion sensitive transistor 510 has three input connections, solution input 520, reference input 530, and diffusion input 540, and a single output connection, diffusion output 550. Diffusion output 550 provides the electrical output signal. Ion sensitive transistor 510 is connected as a pass transistor by applying a reference voltage to reference input 530 and a baseline voltage to diffusion input 540. In this configuration, the voltage drop between diffusion input 540 and diffusion output 550 indicates the ion concentration within the solution that is in contact with solution input 520.

In the preferred embodiment, the baseline signal applied to the diffusion input is a pulsed signal, however this is only one possible preferred embodiment. Other preferred embodiments include using a constant (or other analog signal) at the diffusion input. In all cases the ion concentration response is obtained from the potential difference between the diffusion input and the diffusion output (not from the absolute value of the input and output signals). The sensor response is described in more detail below.

Ion sensitive transistor 510 may be a p-type or an n-type transistor. The preferred embodiments are directed at an ISFET-based sensor, however the embodiments apply to sensors based on other types of ion sensitive transistors without loss of generality.

Ion concentration sensor 500 is capable of measuring the concentration of any ion which causes a threshold drop between diffusion input 540 and diffusion output 550. Preferably, the ion measured is hydrogen, so that ion concentration sensor 500 functions as a pH sensor. The following embodiments are directed at a pH sensor, however the embodiments apply to concentration sensors for other ions without loss of generality.

Note that in some of the following figures the solution input is not shown explicitly on the figure, but is nonetheless present as an ion sensitive portion of the transistor.

Figure 6:
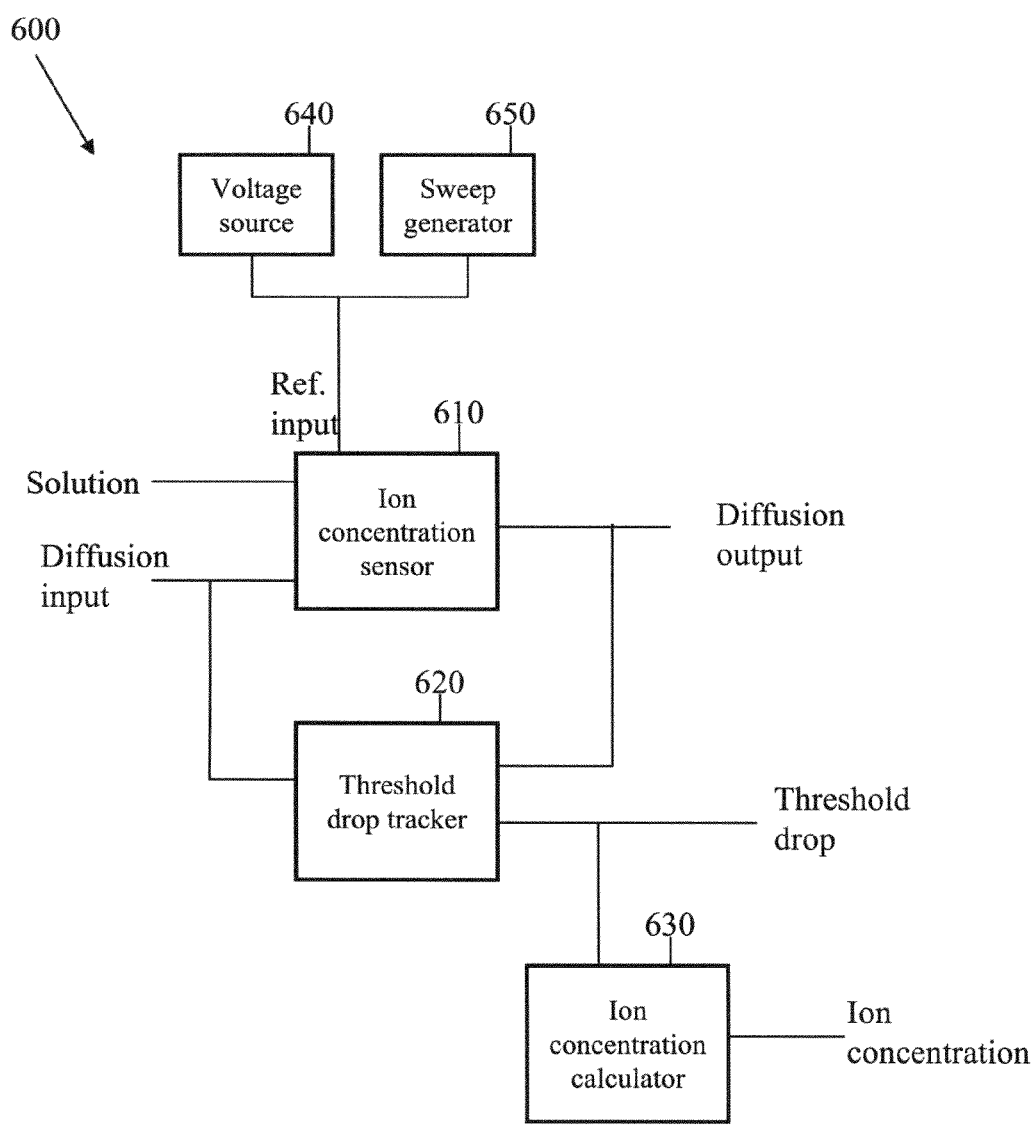

Reference is now made to FIG. 6, which is a simplified block diagram of a second ion concentration sensor, according to a preferred embodiment of the present invention. Ion concentration sensor system 600 consists of ion concentration sensor 610, configured essentially as described above, and one or more of: threshold drop tracker 620, ion concentration calculator 630, voltage source 640, and sweep generator 650.

In the preferred embodiment, threshold drop tracker 620 is connected between the diffusion input and the diffusion output of the ion concentration sensor (the reference and solution inputs are not shown). Threshold drop tracker 620 produces an output signal which tracks the voltage drop between the diffusion input and output, and therefore reflects the ion concentration at the solution input.

Preferably, ion concentration sensor system 600 further includes ion concentration calculator 630, which calculates the ion concentration from the voltage drop between the diffusion input and the diffusion output. Ion concentration calculator 630 provides a numerical indication of the ion concentration. Ion concentration calculator 630 may be connected at the output of threshold drop tracker 620 as shown, or directly between the sensor diffusion input and diffusion output.

Preferably, ion concentration sensor system 600 contains voltage source 640, which provides a stable reference voltage to the reference input In most ISFETs reported in the literature, a drift of the drain current is observed while operating under constant bias conditions of the reference electrode and a constant drain-source voltage. P. A. Hammond, D. Ali, D. R. S. Cumming, in "A Single-Chip pH Sensor Fabricated by a Conventional CMOS Process", in Eurosensors XVI, 2002, hypothesize that the drain current drift occurs because the basic sites on the gate insulator surface are positively charged, so that applying a negative reference voltage attracts the positive charges from the sites, increasing the negative charge at the surface. This, in turn, biases the ISFET further into conduction, increasing the drain current. If the reference voltage is removed, the surface sites regain equilibrium with the solution. Applying a positive voltage drives the protons to the surface, but alters the equilibrium. It has been shown that drain current drift can be compensated for by using a symmetric biasing scheme, with a sequence of positive and negative sweeps applied to the reference electrode.

Preferably, ion concentration sensor system 600 contains sweep generator 650, which applies a sequence of positive and negative voltage sweeps to the reference input.

Figure 7:
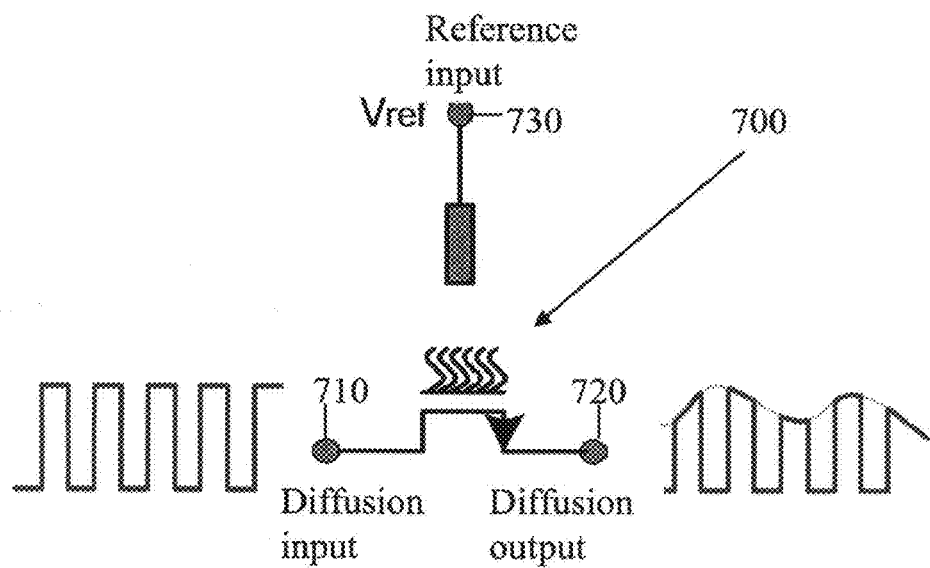

Reference is now made to FIG. 7, which illustrates the response of ion concentration sensor 700 to a square wave baseline signal at diffusion input 710. The square wave signal effectively samples the ion concentration of the solution. Each time the input pulse is high, a $V_T$ drop occurs, reflecting the changes caused by the presence of ions in the solution. The output signal thus consists of a pulsed signal, with the amplitude of each pulse determined by the current ion concentration level.

In the preferred embodiment shown in FIG. 7, the pulsed signal is applied to diffusion input 710 (drain or source). In an alternate preferred embodiment, the pulsed signal is applied to reference input 730, which is commonly the transistor gate. Applying the pulsed signal to the gate may require using longer pulses in order to stabilize the ISFET.

Figure 8:
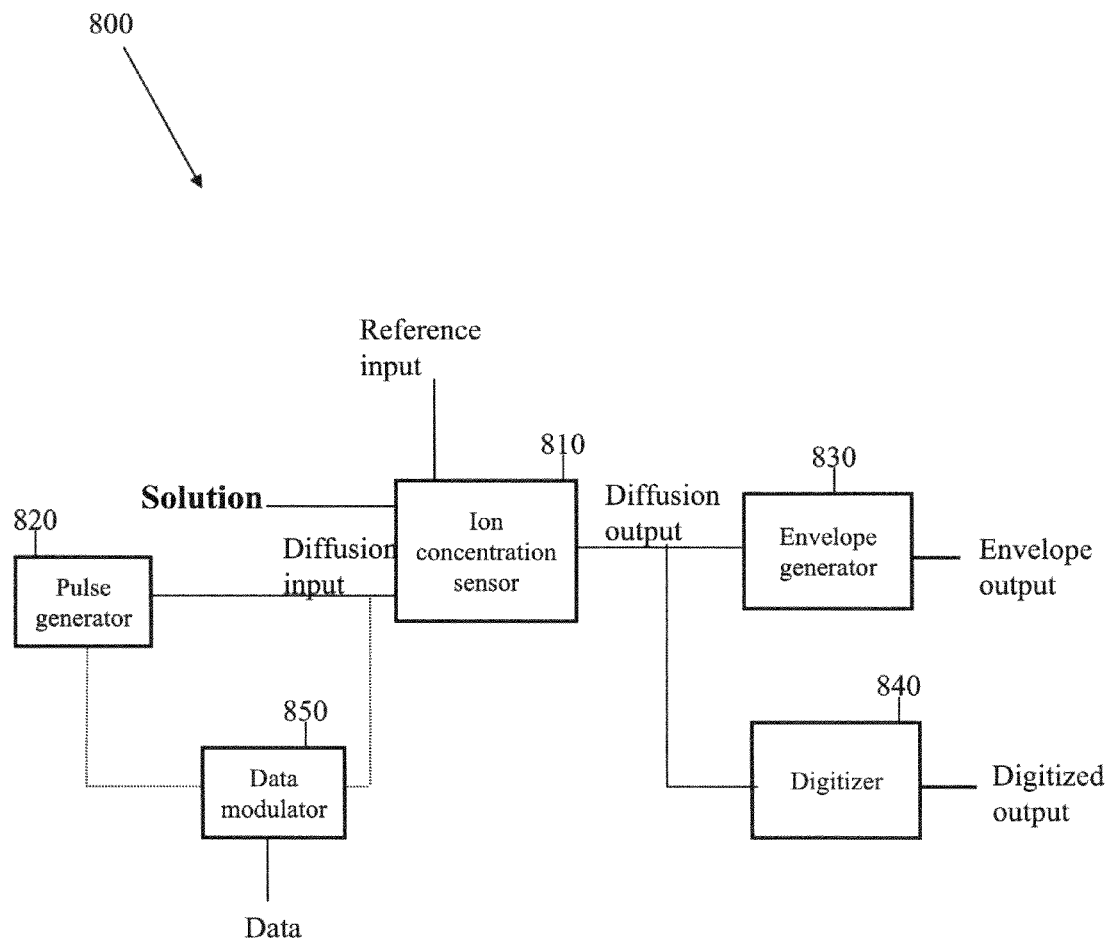

Reference is now made to FIG. 8, which is a simplified block diagram of an ion concentration sensor with a pulsed baseline input signal, according to a preferred embodiment of the present invention. Pulsed ion concentration sensor 800 consists of ion concentration sensor 810, configured essentially as described above, pulse generator 820, and at least one of: envelope generator 830, digitizer 840, and data modulator 850.

Pulse generator 820 generates a pulsed signal, which serves as the baseline signal to the diffusion input of ion concentration sensor 810. The electrical signal at the sensor diffusion output is a pulsed signal, modulated by the ion concentration at the time of each pulse. Preferably, pulse generator 820 is a square wave pulse generator. Note that drain current drift compensation is automatically obtained when the baseline pulsed signal is applied to the transistor gate, eliminating the need to provide a symmetric biasing sequence of positive and negative sweeps.

In the preferred embodiment, pulsed ion concentration sensor 800 contains envelope generator 830, which provides the envelope of the modulated pulsed output signal. Envelope generator 830 effectively produces the output signal which would be provided by an ion concentration sensor with a constant baseline signal. Preferably, envelope generator 830 consists of a low pass filter (LPF).

The pulse amplitude modulation that occurs during the pass transistor operation is similar to the sampling operation at the input to an analog to digital converter (ADC). In the preferred embodiment, pulsed input ion concentration sensor 800 is followed by digitizer 840, which converts the analog level at the peaks of the output pulse to a digital signal. The ion concentration can thus be provided in digital format, without requiring additional sample and hold circuitry.

In the preferred embodiment, the pulsed baseline signal is not input directly to ion concentration sensor 800, but is first modulated with digital data by data modulator 850. The pulsed output signal thus carries both a pH level indication (in the pulse amplitude), and digital data (in the pulse sequence). The need for a separate data line may thus be eliminated for systems which perform both ion concentration sensing and digital data transport. Such systems include biotelemetry systems which transmit pH measurements along with digital data, such as synchronization series, location data, and pixel counts.

In the preferred embodiment, the frequency of the pulsed baseline signal is greater than twice a maximum frequency of the ion concentration fluctuation, which is generally on the order of 10 Hz. The baseline signal frequency is in accordance with the Nyquist sampling theorem, which states that the sampling rate must be at least twice the maximum frequency of the sampled signal in order for the signal to be correctly recovered.

Figure 9:
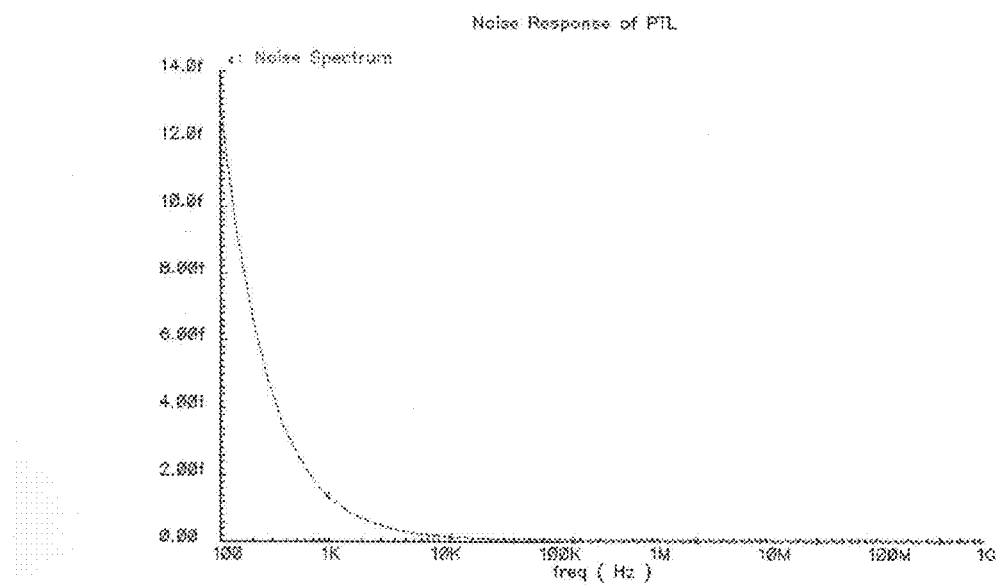

In the case of an ISFET-based ion concentration sensor, sampling at above the Nyquist frequency has the added advantage that the 1/f noise is reduced, due to the high-frequency operation of the FET. As shown in Jakobson and Nemirovsky, ISFETs are strongly influenced by the 1/f noise which occurs at low frequencies. The typical spectral power density of ISFET 1/f noise, derived from simulations, is shown in FIG. 9. At low pulse frequencies the 1/f noise may cause sensor measurement errors. In cases where the 1/f noise is dominant in the sensor output signal, the sampling frequency can be increased beyond the rate that is needed for signal recovery, so as to reduce the noise appearance. The maximal over-sampling rate is defined by the bandwidth limit of the overall system, and the number of switched sensors in the system.

When the pulsed baseline signal is modulated by a data signal, the time between high pulses is not regular, but varies in accordance with the transmitted data. In the preferred embodiment, the maximal time between high pulses at the sensor input is small enough to provide an effective sampling frequency at least equal to the Nyquist frequency. The condition is automatically met in systems which combine n-type and p-type ISFET modulation, where the p-type sensor is modulated by zeros.

Reference is now made to FIG. 10, which is a simplified block diagram of an ion concentration sensor with error compensation, according to a preferred embodiment of the present invention. Ion concentration sensor 1000 is configured essentially as described above, and is connected to error eliminator 1010. Error eliminator 1010 consists of error detector 1020 and subtractor 1030. Error detector 1020, provides an error signal essentially equal to the body effect of the ion sensitive transistor. Subtractor 1010 subtracts the error signal from the electrical signal at the ion concentration sensor's diffusion output, rejecting the influence of the pseudo-reference electrode instability and the body effect as common mode signals. The resulting output signal indicates the ion concentration of the solution and is free of body effect errors.

In standard CMOS applications, body effect limitations require that an ISFET that is configured as a pass-transistor must be a p-type transistor. The reason is that p-type FETs are used is that in n-type devices the bulk is constantly connected to the ground, and thus a potential difference develops between the bulk and the modulated source signal. An ion concentration sensor with error compensation can be constructed from an n-type transistor, without the interference of body effects.

In the preferred embodiment, error detector 1020 consists of a reference transistor, which has a gate, a diffusion input, and a diffusion output. The reference transistor is configured as a pass transistor, and connected in parallel with ion concentration sensor 1000. The reference transistor is a transistor electrically similar to the ion sensitive transistor in ion concentration sensor 1000, but without an ion sensitive portion. The reference transistor response does not contain a component reflecting the ion concentration, but is otherwise similar to that of the ion concentration sensor. When the error signal provided reference transistor is subtracted from the ion concentration sensor response, only the ion-sensitive portion of the response remains. Note that this configuration may also provide temperature compensation when the reference and ion-sensitive transistors have similar dimensions. Preferably, the reference transistor consists of a reference field effect transistor (REFET).

Reference is now made to FIG. 11, which is a simplified circuit diagram of an ion concentration sensor with a REFET-based error eliminator, according to a preferred embodiment of the present invention. The error-compensated ion sensor shown in FIG. 11 has a differential structure, which can be used for both body effect elimination and REFET operation. In case of body effect, the ISFET has to be connected with a common MOSFET. The modulating signal is inputted to both devices, and during the differentiation performed by the subtractor the body effect influence is rejected as a common mode signal. Thus, the output signal primarily contains pH-based fluctuations.

The ion concentration sensor of the above embodiments can form the basis for a dual-mode sensor, which is sensitive to both ion concentration and light intensity. Reference is now made to FIG. 12, which is a simplified block diagram of a first dual-mode sensor, according to a preferred embodiment of the present invention. Dual-mode sensor 1200 consists of ion sensitive transistor 1210, configured as a pass transistor, and light sensitive device 1220, which has a discharge rate indicating the local light intensity. The junction between ion sensitive transistor 1210 and light sensitive device 1220 forms a sensor output 1230, which provides an output signal response dependent on both ion concentration and light intensity. Ion sensitive transistor 1210 may be a p-type or an n-type transistor.

The dual-mode sensor is based on the structure of the Active Pixel Sensor (APS), as described by Z. Zhou, B. Pain, and E. Fossum in "A CMOS imager with on-chip variable resolution for light-adaptive imaging", IEEE International Solid-State Circuits Conference, pp. 174-175, 1998, which is hereby incorporated by reference. Reference is now made to FIGS. 13a and 13b, which are a simplified circuit diagram and an equivalent circuit of an APS. The circuit diagram in FIG. 13a shows APS 1300, consisting of reset transistor M1 (1310), photodiode 1320, source-follow transistor M2 (1330), and switch transistor M3 (1340). FIG. 13b is the equivalent circuit, in which photodiode 1320 is represented by current source 1320.1 and capacitor 1320.2, which are connected in parallel. Current source 1320.1 provides a current that is a function of photon flux during the illumination and the diode area.

APS operation is based on the charge integration mode of photodiode 1320. A pulsed signal is applied to the reset input, to switch APS 1300 between a reset and an integration phase. During the reset phase, photodiode 1320 is reset to a high voltage via transistor M1 (1310). During the integration phase, photodiode 1320 discharges according to:

$$C \cdot \frac{dV(t)}{dt} = -i_{photo} \quad (10)$$

Source follower M2 (1330) acts as a voltage buffer that drives the output. Thus, the light intensity is translated to a linear slope of the output voltage, where a higher illumination results in a lower output voltage level at the end of the integration phase.

M3 (1340) acts as a switch, which connects and disconnects the output signal from the APS output terminal. APS sensor 1300 can thus be incorporated into a sensor array, and switched on and off according to a control signal at the control input.

APS 1300 may contain NMOS transistors (which are more space efficient as they do not require a separate well), or PMOS transistors (which are less area efficient but do not exhibit a body effect).

FIG. 14 presents transient simulation results for a standard APS sensor. The APS circuit was implemented in 0.5 μm CMOS technology with $3V_{P-P}$ voltage supply. FIG. 14 shows that for a standard APS under conditions of constant illumination the slope and the overall voltage change during the integration phase are equal for each cycle. The amplitude of the signal at the beginning and end of the integration phase are equal as well.

In standard APS sensors using an NMOS transistor as reset transistor M1, as is commonly done, results in a reduced reset voltage for the photodiode due to the $V_{T_{M1}}$ the threshold drop of the reset transistor in the pass gate configuration. The photodiode response is therefore limited to a range of $V_{DD}-V_{T_{M1}}$. An additional $V_{T_{M2}}$ drop occurs at the sensor output due to source follower M2 (1330). The threshold drop is considered an undesired limitation on the dynamic range of the APS sensor, in standard digital and mixed-signal design. However, this threshold drop is beneficial for the dual-mode sensor, due to the ion concentration response of the ion sensitive transistor which replaces reset transistor M1 (1310) in the dual-mode sensor.

Reference is now made to FIG. 15, which is a simplified circuit diagram of an ISFET-based dual-mode sensor, according to a preferred embodiment of the present invention. Dual-mode sensor 1500 is configured similarly to the APS shown in FIG. 13a, with ISFET 1510 replacing transistor M1 (1310), to include an ion sensitive component in the sensor response. With a pulsed baseline signal, ion concentration fluctuations are indicated by the peak values of the output signal during the reset phase, and the light intensity is indicated by the rate of fall of the signal during the integration phase.

Reference is now made to FIGS. 16a and 16b, which show the emulated response of an ISFET-based dual-mode sensor (1500) to pH fluctuations, under constant illumination. AC waveforms were applied to the ISFET gate, to emulate the pH-caused fluctuations in the ISFET threshold drop, $V_T$. Changes to the gate voltage are functionally equivalent to a pH induced threshold drop, since the output voltage $V_S$ is a function of the difference between the gate voltage and the threshold drop, $V_G - V_T$, so that changes in $V_T$ can be emulated by changes in $V_G$. The figures show the dual-mode sensor response to 1 $V_{P-P}$ signals at a frequency of 100 Hz, with a sampling rate of 1 KHz.

FIGS. 16a and 16b each present three waveforms, the AC waveforms used to imitate pH fluctuations (upper waveform), the sensor response at the transistor/photodiode junction (middle waveform), and the sensor response at the sensor output (lower waveform). FIG. 16a shows the dual-mode sensor response to a square wave applied to the diffusion input, to control the reset and integration phases. FIG. 16b shows the dual-mode sensor response to a sinusoidal signal applied to the diffusion input.

As shown in FIGS. 16a and 16b, the pH fluctuations modulate the upper bound of the output signal due to the varying threshold drop. The envelope of the output signal follows the shape and magnitude of the changes in the ISFET threshold drop, $V_T$. The light intensity is indicated in the sensor output by the rate of fall of the pulsed output signal. For a given illumination level, the slope and magnitude of the output signal drop over a single cycle are constant, and indicative of the light intensity. The dual-mode sensor response is thus a measure of both ion concentration (in this case pH) and light intensity. Note that although the signal level may be reduced by a certain negative gain in source-follower transistor M2 (1530) at the sensor output, the general properties of the sensor response are preserved, and remain indicative of ion concentration and light intensity.

Reference is now made to FIG. 17, which is a simplified block diagram of a second dual mode sensor, according to a preferred embodiment of the present invention. Dual-mode sensor 1700 consists of ion sensitive transistor 1710, configured essentially as described above, and light sensitive device 1720. Dual-mode sensor may further contain at least one of: amplifier 1730, switch 1740, threshold drop tracker 1750, envelope generator 1760, slope measurer 1770, and fall detector 1780. Envelope generator 1760, slope measurer 1770, and fall detector 1780 are shown as following switch 1740, but any or all may follow amplifier 1730, or be connected directly to the junction between ion sensitive transistor 1710 and light sensitive device 1720. Preferably, ion sensitive transistor 1710 consists of an ISFET. Preferably, light sensitive device 1720 consists of a photodiode.

In the preferred embodiment, dual-mode sensor 1700 contains amplifier 1730 which amplifies the electrical signal at the junction between ion sensitive transistor 1710 and light sensitive device 1720. Amplifier 1730 performs a function similar to source-follower transistor M2 (1340).

In the preferred embodiment, dual-mode sensor 1700 contains switch 1740 which switches dual-mode sensor 1700 on and off. Switch 1740 performs a function similar to transistor M3 of FIGS. 13a and 13b. Switch 1740 generally follows amplifier 1730, but may be connected directly to the junction between ion sensitive transistor 1710 and light sensitive device 1720.

Dual-mode sensor 1700 preferably contains threshold drop tracker 1750 and/or envelope generator 1760, which each provide signals indicative of the ion concentration. Threshold drop tracker 1750 is connected between the diffusion input and the diffusion output of ion sensitive transistor 1710. Threshold drop tracker 1750 tracks the voltage drop the diffusion input and the diffusion output, similarly to the threshold drop tracker of FIG. 6. Envelope generator 1760 follows dual mode sensor 1700, and provides the envelope of the electrical signal at the sensor output.

Dual-mode sensor 1700 preferably contains slope measurer 1770 and/or fall detector 1780, which each provide signals indicative of the light intensity. Slope measurer 1770 determines the rate of fall of the electrical signal at the sensor output. Fall detector 1780 determines the amplitude drop of the sensor output signal over a single cycle.

The dual-mode sensor capability of simultaneously monitoring images and ion concentration (i.e. pH) levels is useful in a wide variety of fields. The dual-mode sensor may be incorporated into biomedical sensors. During neurosurgery, for example, measurement of pH levels may be correlated with image monitoring of the brain surface, to locate and identify trauma injuries. A biomedical sensor based on the dual-mode sensor may enable rapid diagnostics in the emergency room, monitoring patient conditions during an operation, and continuous monitoring during hospital admission and later therapy. Additional biomedical embodiments are presented below.

In the preferred embodiment, the dual-mode sensor is incorporated into a gastro-intestinal pill, which measures X-ray intensity and pH within a digestive tract. Both these measurements are of great importance in gastro-intestinal tract monitoring. A gastro-intestinal sensor can be used to identify injured areas, such as blood spots. The gastro-intestinal sensor may also be useful for positioning purposes. Images obtained by a gastrointestinal sensor may replace the standard X-ray monitoring which is currently performed during traditional gastroscopy, while minimizing the harmful and inconvenient conditions for the patient. Providing a dual-mode sensor in a single biotelemetry pill may enable efficient and convenient monitoring.

Reference is now made to FIG. 18, which is a simplified block diagram of a test device for performing ion concentration and image analysis of a sample, according to a preferred embodiment of the present invention. Test device 1800 contains at least one dual-mode sensor 1810, ion concentration analyzer 1820, image analyzer 1830, and correlator 1840. The dual-mode sensors consist of a light sensitive device connected to an ion sensitive transistor configured as a pass transistor, as described above. Data is provided by dual-mode sensors 1810 to both ion concentration analyzer 1820 and image analyzer 1830. Ion concentration analyzer 1820 extracts the ion sensitive component from the provided data, and analyzes ion concentration in the sample. Image analyzer extracts the light sensitive component from the provided data, and analyzes the optical data. Correlator 1840 correlates the analysis results provided by from ion concentration analyzer 1820 with those of image analyzer 1830, to obtain information about the sample under test. Correlator 1840 may also correlate the analysis results with externally provided data, such as images from a microscope.

In the preferred embodiments, one or more of the components of test device 1800 has digital signal processing (DSP) capabilities, to facilitate processing of the sensed data.

In a first preferred embodiment, the dual-mode sensor is incorporated into a cell identification device, such as a fluorescent activated cell sorter (FACS), for identifying cells within a sample in accordance with a fluoroscopic tag associated with the cell and the sample pH. Cell recording and identification is an important research issue in biochemistry, neurophysiology and other biomedical fields. One example of a dual-mode sensor embodiment is the Neuronal Recording System described by E. Perelman and R. Ginosar in "Neural Processors: VLSI Architectures for Computational Interfaces with Biological Neural Networks", Technion, technical report, 2003. Monitoring neuronal interfaces is generally performed by metal recording sites on a class substrate, or by ISFET sensors on silicon. Image sensors are used for obtaining continuous supervision of the functionality, structure and interconnection of a neural network which is grown on a silicon chip or located in solution. Combining dual-mode sensors in 10-20 μm grids will enable monitoring both these parameters with a single sensor array, and may provide a platform for high-performance recording systems for neuronal monitoring.

In another preferred embodiment, the dual-mode sensor is incorporated into a sperm mobility measurer, which may be utilized during fertility studies. The mobility of the sperm cells is obtained by processing sequences of images of a sperm sample. The dual-mode sensor provides the sequence of images along with pH measurements. The sperm mobility measurer also contains an image analyzer, which analyzes the sequence of images to identify sperm motion and/or shape, and a correlator, which correlates the sperm motion with the pH measurements. The combination of chemical and image sensing abilities may be used to derive additional physiological parameters by data processing.

The above described ion concentration and dual-mode sensors are well suited to array-type sensors, where the small size of the sensor is of great importance. The sensors may be formed into arrays without additional readout circuitry, thereby enabling the fabrication of sensor arrays with reduced area and simple control.

Reference is now made to FIG. 19, which is a simplified block diagram of a sensor array, in accordance with a preferred embodiment of the present invention. Sensor array is formed from a grid of sensors, 1910.0 to 1910.m+n, each having a solution input, a reference input, a diffusion input, and an output. Note that the arrangement of the sensor grid shown in FIG. 19 is for illustration purposes only, and is not limiting.

Sensor array 1900 may be composed of ion concentration sensors, of dual-mode sensors, or of a combination of ion concentration and dual-mode sensors. Preferably, when a dual-mode sensor is used, the sensor diffusion input serves as the control input, for switching each sensor between the reset and integration phases, and the reference input is connected to a reference voltage.

Preferably, each sensor in sensor array 1900 has a respective switch, which connects and disconnects the sensor from the sensor array output, in accordance with a control signal. In the preferred embodiment, sensor array 1900 also contains a switching device, for controlling the respective switches. The switching device may consist of an analog switch, such as those commonly used in array-type monitoring systems.

In the preferred embodiment, sensor array 1900 is formed from an array of p-type sensors, having a common reference electrode constantly connected to ground. A high-low-high pulse is sequentially introduced to the drain of each of the sensors, resulting in an output signal modulated by the threshold voltage drop of each sensor.

When the dual-mode sensor is incorporated into a sensor array, the reference voltage is common to all the ion sensitive transistors in the array, and is constantly biased. The pulsed reset signal is therefore preferably applied to the transistor drain, while the gate is constantly kept high (for n-type sensors).

Further embodiments of the dual-mode sensor are expected to emerge with an improvement in ISFET fabrication techniques. Most of the ISFET sensors fabricated today are relatively big, with sensing area of hundreds of square microns. These dimensions are dictated by the requirement for good measurement statistics for the ion interactions over a limited area, and by the current limitations of ISFET fabrication techniques in standard CMOS technology.

FIG. 20 presents the layout of a prior art 10×10 μm APS pixel in 0.35 μm CMOS technology, as shown by A. Morgenshtein and I. Bruk in "A 128×128 CMOS Startracker based on APS", Technion, technical report, 2002. The tendency of the APS design is to minimize the area of M1-M3 transistors, while increasing the illumination-sensitive area of the photodiode. If the reset transistors are replaced by relatively large ISFETs, the area which is insensitive to light is increased and the fill factor of the pixel is decreased.

CMOS imagers based on APS sensors have already been achieved with a 10×10 μm pixel size, and sensors with a pixel size of less than 5×5 μm have been fabricated under research conditions. Fabrication of CMOS ISFETs currently involves sophisticated post-processing, often followed by small-scale mask or manual layer application. As the fabrication techniques for small-size ISFET sensors improve, dual-mode sensors will become increasingly useful for the many applications which require sensors of at most 10×10 μm size. Reducing the ISFET sensor size, preferably to dimensions of several square microns, will enable integrating the dual-mode sensor into an APS pixel. Note that the dual-mode sensor has two mutually reducing dynamic ranges. The first dynamic range is for the pH measurements, and is defined by the sensitivity of the ISFET. The pH dynamic range is commonly up to 100 mV (2 pH units) for clinical applications and up to 600 mV (10 pH units) for general applications. The second dynamic range is for the image sensor, and is dependent on supply voltage and threshold drops of the transistors. The image sensor dynamic range is generally up to 2V in 0.35 μm technology, and tends to decline with each new generation of sensors.

The two dynamic range limitations raise two possible constraints: (a) a high dynamic range of the pH measurement reduces the dynamic range of the imager, (b) a low dynamic range of the ISFET sensor reduces the immunity of the pH measurement to Fixed Pattern Noise (FPN). FPN is a function of on-chip parameter fluctuations in the array devices. FPN can manifest itself in threshold voltage fluctuations of tens of millivolts in identical FETs, conductivity fluctuations, and so forth. In current image sensors, this problem is partially solved by applying Correlated Double Sampling (CDS) circuits in the readout of the sensor. The CDS technique is of increased importance for pH measurement with a limited dynamic range.

An additional solution to the dynamic range issues is performing post-fabrication calibration of the sensor array, in order to derive parameters of importance for each pixel, and adjusting of the measurements by data processing. Although this calibration makes production and maintenance more complex and expensive, such calibration is widely and successfully used in other sensor fields, and can be effectively applied to the dual-mode sensor.

Reference is now made to FIG. 21, which is a simplified flowchart of a method for producing a signal reflective of the ion concentration within a solution, according to a preferred embodiment of the present invention. The method utilizes an ion sensitive transistor having an ion sensitive portion, a gate, a diffusion input, and a diffusion output. Preferably, the ion sensitive transistor is an ISFET.

In step 2100 the ion sensitive transistor is configured as a pass transistor. In step 2110 the solution being tested is applied to the ion sensitive portion of the transistor. Finally, in step 2120, an electrical signal indicating the ion concentration is obtained.

Preferably the method contains the further step of detecting a voltage drop between the first diffusion input and the first diffusion output. The detected voltage drop is indicative of the ion concentration.

Preferably the method contains the further step of generating an envelope of electrical signals at the diffusion output.

Reference is now made to FIG. 22, which is a simplified flowchart of a method for configuring the ion sensitive transistor, according to a preferred embodiment of the present invention. The ion sensitive transistor is configured as a pass transistor as follows. In step 2200, a reference voltage is provided to the transistor gate. In step 2210, a baseline signal is input to the diffusion input.

The baseline signal may consist of a pulsed signal. Preferably the method contains the further step of modulating the pulsed signal with digital data. Preferably, the frequency of the pulsed signal is set to be greater than the Nyquist frequency, based on the rate of change of the solution ion concentration.

Preferably, the level of the reference voltage is essentially stable. A sequence of positive and negative sweeps may be applied to the reference input, to reduce drain current drift, as discussed above.

Reference is now made to FIG. 23, which is a simplified flowchart of a method for error elimination, according to a preferred embodiment of the present invention. Error factors, such as body and temperature effects, may be eliminated or reduced by pairing the ion sensitive transistor with a reference transistor. The reference transistor is configured similarly to the ion sensitive transistor, with the reference voltage to the reference transistor's reference input and the baseline signal applied to the reference transistor's diffusion input.

In step 2300 the reference transistor is configured in parallel with the ion sensitive transistor. In step 2310, the error signal at the reference transistor's diffusion output is subtracted from output signal at the ion sensitive transistor's diffusion output.

Reference is now made to FIG. 24, which is a simplified flowchart of a method for producing a signal simultaneously reflective of light intensity and of ion concentration, according to a preferred embodiment of the present invention. The current method is similar to the method of FIG. 23, with the additional step of connecting the diffusion output of the ion sensitive transistor to a light sensitive device having a discharge rate indicative of the light intensity (step 2405). The electrical signal obtained in step 2430, indicates both light intensity and ion concentration.

Preferably, the light sensitive device is a photodiode.

Preferably the method contains the further step of detecting a voltage drop between the first diffusion input and the first diffusion output, which is indicative of the ion concentration.

Preferably the method contains the further step of isolating a light-responsive component of the electrical signal. The light intensity may be derived from the rate of change of the output signal and/or the amplitude drop of the output signal over a single cycle.

Reference is now made to FIG. 25, which is a simplified flowchart of a method for performing ion concentration and image analysis of a sample, according to a preferred embodiment of the present invention. The method is performed on ion concentration and image data provided by at least one dual-mode sensor. Each of the dual-mode sensors consists of a light sensitive device connected to an ion sensitive transistor configured as a pass transistor, as described above. In step 2500 the ion concentration data is analyzed. In step 2510, the image data is analyzed. In step 2520, the analyzed ion concentrations are correlated with the analyzed images.

Preferably, the method contains the further step of correlating the ion concentration and image data with externally provided data. The externally provided data may be optical data, such as one or more digitized images from a microscope.

EXAMPLES

The performance of ion concentration sensor presented above was verified by simulations, and by measurements of a test chip. FIG. 26 presents simulation results of the transient response of an ISFET in pass-transistor mode to a 400 mVp-p sinusoidal input. The sinusoidal signal is applied to the ISFET gate at a frequency of 1 KHz, and is sampled by square pulses at 100 KHz applied to the diffusion input The output waveform shows that after the immediate sampling and $V_T$ drop, there is a slow drift of the signal while the sampling pulse is high. The signal drift is caused by the fact that after the transistor stops conducting there is still a low leakage current, known as the subthreshold current, which continues to charge the output node. The subthreshold current is very low, and its contribution to each sample value is similar, due to the similar period of the pulse. Increasing the operating frequency may reduce the effect of subthreshold current on the measurement.

FIGS. 27 and 28 show the test chip response to pH fluctuations. FIG. 27 shows the measured response of an ISFET-based ion sensitivity sensor to a triangular signal. FIG. 28 shows the sensor response to a sinusoidal signal, measured simultaneously by n-type and p-type FETs. The operational concept of the p-type pass-transistor is similar to the n-type transistor, however the threshold drop occurs at a low voltage, so that the output level is $V_T$ rather than the expected 0V.

The $V_T$ fluctuations can be derived in analog form from a set of samples by connecting an LPF to the ISFET diffusion output. FIG. 29a presents measurements of the pass-transistor response to a sinusoidal input, while FIG. 29b shows the resulting output signal after filtering by the LPF.

Measurements were performed using commercial ISFET sensors to assure proper operation in real ion sensitivity sensors. During the experiment, the ion sensitivity sensor was placed in pH7, pH4 and pH9 solutions. FIGS. 30a and 30b show the response of an ion concentration sensor sampling a sinusoidal and triangular signal respectively.

The above embodiments present an ion concentration sensor based on an ion sensitive transistor configured as a pass transistor. Potential uses are foreseen in a large number of fields, including biomedical monitoring devices, lab-on-chip, biological and medical research equipment, agriculture, food industry, and geological measurements. The ion sensitivity is manifested as a threshold voltage drop, which is considered a problematic effect in logic design but appears to be useful in pH sensing. The removal of a readout interface at the sensor level can contribute to simplified design and operation of pH sensors for biotelemetry and miniaturized clinical equipment. The readout-free structure of the ion concentration sensor increases the potential for integrating the sensor into high-resolution sensor arrays.

The above embodiments also present a dual-mode sensor, which is based upon integrating an ion sensitive transistor into an APS image sensor. The dual-mode sensor design is attractive for the use in array-type systems with multiple-mode sensing, for various monitoring applications.

It is expected that during the life of this patent many relevant transistors, sensors, sensor arrays, photodiodes, light sensitive devices, and biomedical sensors will be developed and the scope of the terms "transistor", "sensor", "sensor array", "photodiode", "light sensitive device", and "biomedical sensor" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An ion concentration sensor, for producing a signal reflective of the ion concentration within a solution, comprising:
   an ion sensitive transistor comprising:
      a solution input, organized for contact with said solution;
      a first reference input;
      a diffusion input; and
      a diffusion output;
   said ion sensitive transistor being connected as a pass transistor, such that said diffusion output provides an electrical signal indicating an ion concentration in said solution.

2. An ion concentration sensor according to claim 1, further comprising a threshold drop tracker connected between said diffusion input and said diffusion output, for obtaining said electrical signal as a voltage drop between said diffusion input and said diffusion output.

3. An ion concentration sensor according to claim 1, further comprising an ion concentration calculator, for calculating said ion concentration from a voltage drop between said diffusion input and said diffusion output.

4. An ion concentration sensor according to claim 1, wherein said ion is a hydrogen ion.

5. An ion concentration sensor according to claim 1, wherein said ion sensitive transistor comprises an ion sensitive field effect transistor (ISFET).

6. An ion concentration sensor according to claim 1, wherein said ion sensitive transistor comprises a p-type transistor.

7. An ion concentration sensor according to claim 1, wherein said ion sensitive transistor comprises an n-type transistor.

8. An ion concentration sensor according to claim 1, further comprising a pulse source, for applying a pulsed signal to said diffusion input.

9. An ion concentration sensor according to claim 8, wherein said pulse source comprises a square wave generator.

10. An ion concentration sensor according to claim 8, further comprising an envelope generator for providing an envelope of said electrical signal.

11. An ion concentration sensor according to claim 10, wherein said envelope generator comprises a low pass filter (LPF).

12. An ion concentration sensor according to claim 8, wherein a frequency of said pulsed signal is greater than twice a maximum frequency of a rate of change of said ion concentration.

13. An ion concentration sensor according to claim 8, further comprising a data source, for modulating said pulsed signal with digital data.

14. An ion concentration sensor according to claim 1, further comprising a digitizer, for converting said electrical signal to digital format.

15. An ion concentration sensor according to claim 8, further comprising a digitizer, for converting said electrical signal to digital format.

16. An ion concentration sensor according to claim 1, further comprising a sweep generator, for applying a sequence of positive and negative voltage sweeps to said reference input.

17. An ion concentration sensor according to claim 1, further comprising a voltage source, for applying a stable reference voltage to said reference input.

18. An ion concentration sensor according to claim 1, further comprising an error eliminator comprising:
    an error detector, for providing an error signal essentially equal to a body effect of said ion sensitive transistor; and
    a subtractor, for subtracting said error signal from said electrical signal.

19. An ion concentration sensor according to claim 1, wherein said error detector comprises a reference transistor having a second reference input, a second diffusion input, and a second diffusion output, said reference transistor being configured as a pass transistor and connected in parallel with said ion sensitive transistor.

20. An ion concentration sensor according to claim 19, wherein said reference transistor comprises a reference field effect transistor (REFET).

21. A dual-mode sensor, for simultaneous measurement of the intensity of a light and the concentration of an ion in a solution, comprising:
    a light sensitive device, having a discharge rate indicative of said light intensity; and
    an ion sensitive transistor associated with said light sensitive device, comprising:
        a solution input, organized for contact with said solution;
        a reference input;
        a diffusion input; and
        a diffusion output;
    and
    a sensor output, connected to said diffusion output and to an output of said light sensitive device;
    said ion sensitive transistor being connected as a pass transistor, such that said sensor output provides an electrical signal indicating the intensity of a light and of an ion concentration in said solution.

22. A dual-mode sensor according to claim 21, wherein said ion sensitive transistor comprises an ISFET.

23. A dual-mode sensor according to claim 21, wherein said ion sensitive transistor comprises an n-type transistor.

24. A dual-mode sensor according to claim 21, wherein said ion sensitive transistor comprises a p-type transistor.

25. A dual-mode sensor according to claim 21, wherein said light sensitive device comprises a photodiode.

26. A dual-mode sensor according to claim 21, further comprising an amplifier associated with said sensor output, for amplifying said electrical signal.

27. A dual-mode sensor according to claim 26, further comprising a switch associated with said amplifier, for connecting and disconnecting said sensor output in accordance with a control signal.

28. A dual-mode sensor according to claim 21, further comprising a switch associated with said sensor output, for connecting and disconnecting said sensor output in accordance with a control signal.

29. A dual-mode sensor according to claim 21, further comprising an envelope generator associated with said sensor output, for providing an envelope of said electrical signal.

30. A dual-mode sensor according to claim 21, further comprising a threshold drop tracker connected between said diffusion input and said diffusion output, for obtaining said electrical signal as a voltage drop between said diffusion input and said diffusion output.

31. A dual-mode sensor according to claim 21, further comprising a slope measurer associated with said sensor output, for determining a rate of change of said electrical signal.

32. A dual-mode sensor according to claim 21, further comprising a fall detector associated with said sensor output, for determining an amplitude drop of said electrical signal over a single cycle.

33. A dual-mode sensor according to claim 21, said dual-mode sensor being for incorporation within a biomedical sensor.

34. A dual-mode sensor according to claim 33, wherein said biomedical sensor is constructed for use in a gastrointestinal environment, for measuring X-ray intensity and pH (potential of Hydrogen) within a digestive tract.

35. A dual-mode sensor according to claim 33, wherein said biomedical sensor comprises a sperm mobility measurer, said sperm mobility measurer comprising:
    an image analyzer, for analyzing a sequence of images of a sperm sample to identify sperm motion; and
    a correlator associated with said image analyzer, for correlating said sperm motion with a pH measurement.

36. A dual-mode sensor according to claim 33, wherein said biomedical sensor comprises a cell identification device, for identifying cells within a sample in accordance with a fluoroscopic tag associated with said cell and the pH of said sample.

37. A test device for performing ion concentration and image analysis of a sample, comprising:
    at least one dual-mode sensor, each of said dual-mode sensors comprising:
        a light sensitive device, having a discharge rate indicative of said light intensity; and
        an ion sensitive transistor associated with said light sensitive device, comprising:
            a solution input, organized for contact with said solution;
            a reference input;
            a diffusion input; and
            a diffusion output;
        and
        a sensor output, connected to said diffusion output and to an output of said light sensitive device;

said ion sensitive transistor being connected as a pass transistor, such that said sensor output provides an electrical signal indicating the intensity of a light and of an ion concentration in said solution;

an ion concentration analyzer associated with said at least one dual-mode sensor, for analyzing ion concentration data obtained from said dual-mode sensors;

an image analyzer associated with said at least on dual-mode sensor, for analyzing a optical data obtained from said dual-mode sensors; and a correlator associated with said ion concentration analyzer and said image analyzer, for correlating said analyzed ion concentrations with said analyzed images.

38. A test device according to claim 37, comprising digital signal processing (DSP) functionality.

39. A test device according to claim 37, wherein said correlator is further operable to correlate said analyzed ion concentrations and said analyzed images with externally provided data.

40. A test device according to claim 39, wherein said externally provided data comprises optical data.

41. A sensor array, comprising:
an array of dual-mode sensors, each of said dual-mode sensors comprising:
  a light sensitive device, having a discharge rate indicative of said light intensity; and
  an ion sensitive transistor associated with said light sensitive device, comprising:
    a solution input, organized for contact with said solution;
    a reference input;
    a diffusion input; and
    a diffusion output;
  and
  a sensor output, connected to said diffusion output and to an output of said light sensitive device;
each of said ion sensitive transistors being connected as a pass transistor, such that a respective sensor output provides an electrical signal indicating the intensity of a light and of an ion concentration in said solution in the vicinity of said sensor.

42. A sensor array according to claim 41, wherein each of said dual mode sensors further comprises a respective switch, for connecting and disconnecting a respective sensor output in accordance with a control signal.

43. A sensor array according to claim 42, further comprising a switching device for controlling said switches.

44. A sensor array, comprising:
an array of ion concentration sensors, each of said ion concentration sensors comprising:
  a solution input, organized for contact with said solution;
  a first reference input;
  a diffusion input; and
  a diffusion output;
said ion sensitive transistor being connected as a pass transistor, such that said diffusion output provides an electrical signal indicating an ion concentration in said solution.

* * * * *